(12) United States Patent
Seifert et al.

(10) Patent No.: US 11,376,039 B2
(45) Date of Patent: Jul. 5, 2022

(54) INTERVENTIONAL MEDICAL SYSTEMS AND ASSOCIATED ASSEMBLIES

(71) Applicant: Medtronic, Inc., Minneapolis, MN (US)

(72) Inventors: Kevin R. Seifert, Forest Lake, MN (US); Vania Lee, Circle Pines, MN (US); Linda L. Franke, Blaine, MN (US); Lonnie D. Ronning, Coon Rapids, MN (US); Dina L. Williams, Andover, MN (US); Michael D. Eggen, Chisago City, MN (US); Carla C. Pfeiffer, Anoka, MN (US)

(73) Assignee: Medtronic, Inc., Minneapolis, MN (US)

(*) Notice: Subject to any disclaimer, the term of this patent is extended or adjusted under 35 U.S.C. 154(b) by 906 days.

(21) Appl. No.: 15/940,259

(22) Filed: Mar. 29, 2018

(65) Prior Publication Data
US 2018/0280057 A1  Oct. 4, 2018

Related U.S. Application Data

(60) Provisional application No. 62/574,424, filed on Oct. 19, 2017, provisional application No. 62/479,034, filed on Mar. 30, 2017.

(51) Int. Cl.
*A61B 17/34* (2006.01)
*A61N 1/362* (2006.01)
(Continued)

(52) U.S. Cl.
CPC .......... *A61B 17/3468* (2013.01); *A61N 1/362* (2013.01); *A61N 1/3756* (2013.01);
(Continued)

(58) Field of Classification Search
CPC ...... A61B 17/3468; A61B 2017/00486; A61B 2017/00292; A61N 1/3756; A61N 1/362; A61N 1/37512
See application file for complete search history.

(56) References Cited

U.S. PATENT DOCUMENTS 5,261,916 A  11/1993  Engeleson
5,304,195 A   4/1994  Twyford, Jr. et al.
(Continued)

FOREIGN PATENT DOCUMENTS

WO  2007067231 A1  6/2007

OTHER PUBLICATIONS (PCT/US2018/025312) PCT Notification of Transmittal of the International Search Report and the Written Opinion of the International Searching Authority, dated Jun. 7, 2018, 10 pages.

*Primary Examiner* — Elizabeth Houston
*Assistant Examiner* — Michael G Mendoza
(74) *Attorney, Agent, or Firm* — Shumaker & Sieffert, P.A.

(57) ABSTRACT

A tethering assembly for securing a medical device includes a shaft and a wire that extends in sliding engagement within a proximal lumen, a channel, and a distal receptacle of the shaft. A retainer zone of the shaft, through which the channel extends, stops a transition segment of the wire, which extends between a proximal and a distal segment of the wire, from moving into the shaft receptacle, thereby restraining a distal-most tip of the wire from moving through a distal-most opening of the receptacle. When a projecting member of the device has entered a secure zone of the receptacle, via movement through the distal-most opening and a tapering passageway thereof, the distal-most tip of the wire, which may be spring-biased, can move distally into the passage-
(Continued)

way so that the tip blocks the projecting member from moving distally, back through the passageway.

18 Claims, 18 Drawing Sheets

(51) Int. Cl.
    *A61N 1/375*     (2006.01)
    *A61B 17/00*     (2006.01)

(52) U.S. Cl.
    CPC ............ *A61N 1/37512* (2017.08); *A61B 2017/00292* (2013.01); *A61B 2017/00486* (2013.01)

(56) References Cited

U.S. PATENT DOCUMENTS

| | | | |
|---|---|---|---|
| 5,350,397 A | 9/1994 | Palermo et al. | |
| 5,895,391 A | 4/1999 | Farnholtz | |
| 6,156,055 A | 12/2000 | Ravenscroft | |
| 6,277,125 B1 | 8/2001 | Barry et al. | |
| 6,506,205 B2 | 1/2003 | Goldberg et al. | |
| 6,953,473 B2 | 10/2005 | Porter | |
| 7,226,466 B2 | 6/2007 | Opolski | |
| 7,473,266 B2 | 1/2009 | Glaser | |
| 7,650,186 B2 | 1/2010 | Hastings | |
| 8,364,280 B2 | 1/2013 | Marnfeldt | |
| 8,504,156 B2 | 8/2013 | Bonner | |
| 8,615,310 B2 | 12/2013 | Khairkhahan | |
| 9,220,906 B2 | 12/2015 | Griswold | |
| 9,526,522 B2 | 12/2016 | Wood | |
| 10,080,888 B2 | 9/2018 | Kelly | |
| 2012/0041470 A1* | 2/2012 | Shrivastava | A61B 17/1219 606/200 |
| 2012/0172891 A1 | 7/2012 | Lee | |
| 2014/0180306 A1 | 6/2014 | Grubac | |
| 2014/0200462 A1 | 7/2014 | Stalker | |
| 2014/0207149 A1 | 7/2014 | Hastings | |
| 2014/0257324 A1 | 9/2014 | Fain | |
| 2015/0051609 A1 | 2/2015 | Schmidt | |
| 2015/0051610 A1 | 2/2015 | Schmidt | |
| 2015/0051611 A1 | 2/2015 | Schmidt | |
| 2015/0094735 A1 | 4/2015 | Ward | |
| 2016/0067446 A1 | 3/2016 | Klenk | |
| 2016/0220829 A1 | 8/2016 | Wood | |
| 2016/0243355 A1 | 8/2016 | Wood | |
| 2016/0263372 A1 | 9/2016 | Wood | |
| 2017/0043158 A1 | 2/2017 | Kelly | |
| 2017/0119999 A1* | 5/2017 | Kelly | A61N 1/37205 |
| 2017/0136231 A1 | 5/2017 | Kelly et al. | |
| 2018/0028805 A1 | 2/2018 | Anderson | |
| 2018/0071518 A1 | 3/2018 | Drake | |

\* cited by examiner

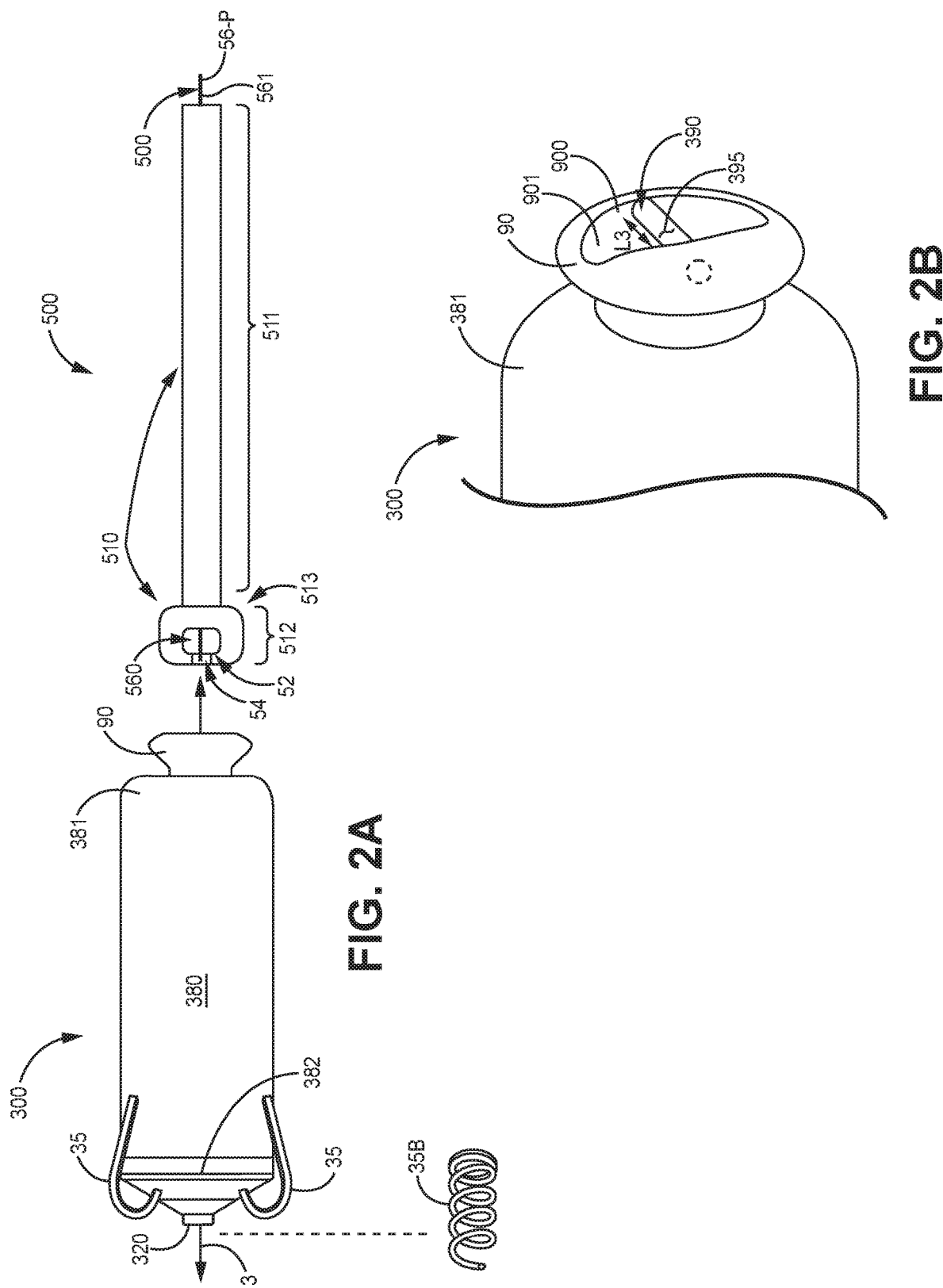

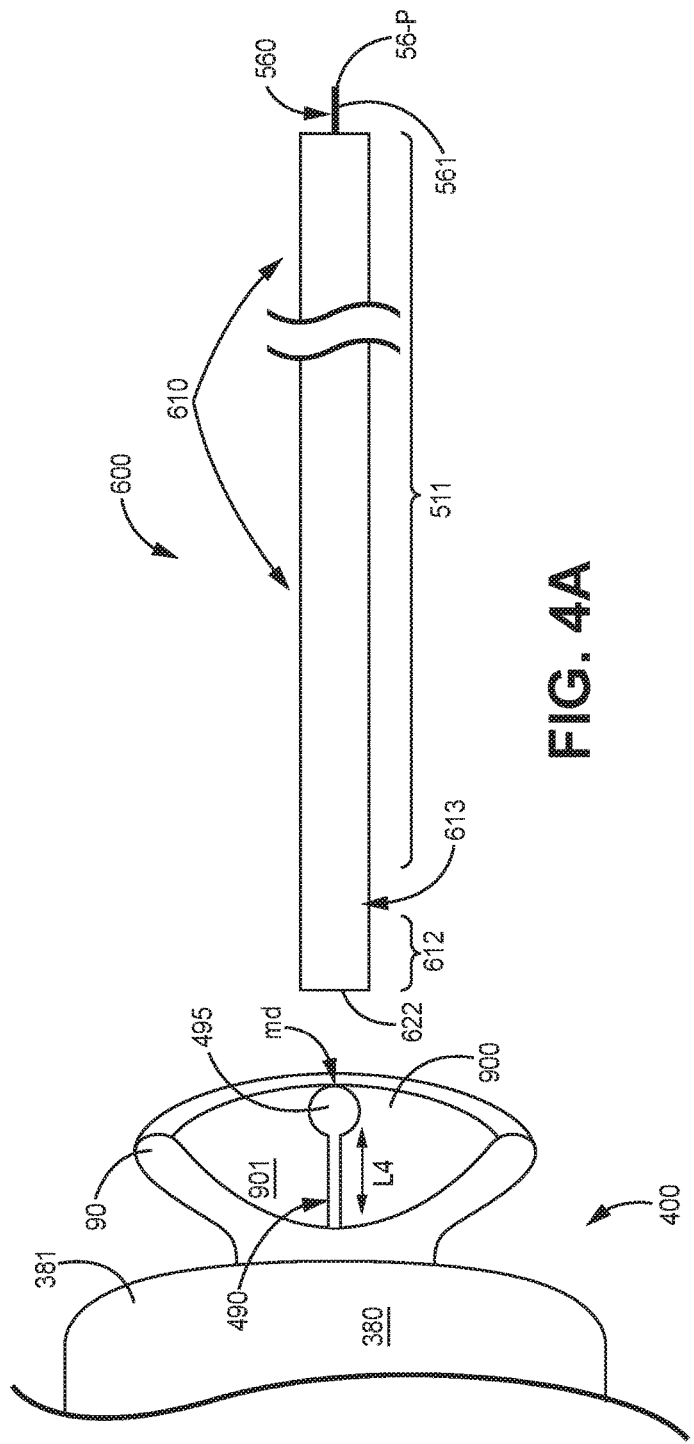
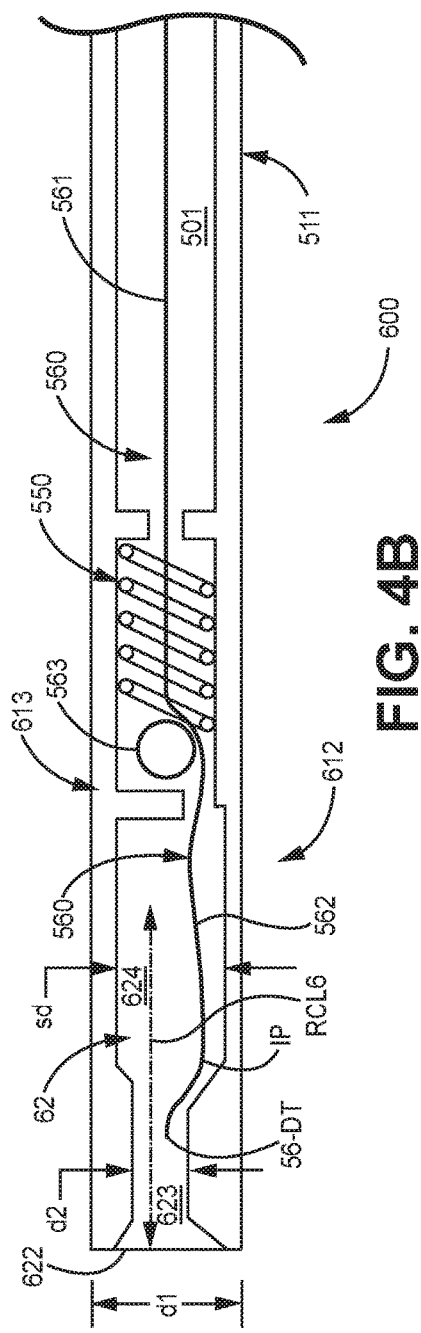
FIG. 4A
FIG. 4B

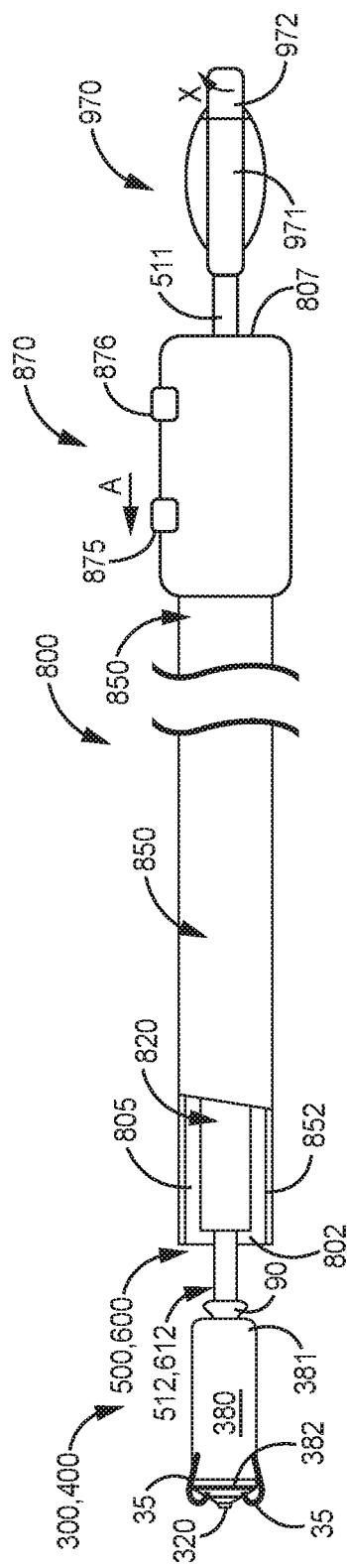
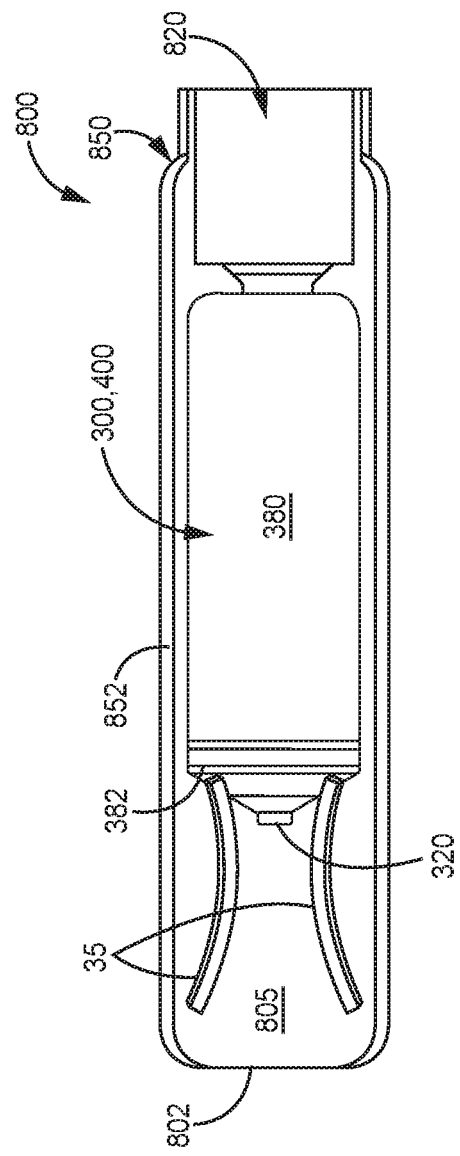
FIG. 5A
FIG. 5B

INTERVENTIONAL MEDICAL SYSTEMS AND ASSOCIATED ASSEMBLIES

RELATED APPLICATIONS

This application claims the benefit of U.S. Provisional Application No. 62/479,034, filed Mar. 30, 2017, and U.S. Provisional Application No. 62/574,424, filed Oct. 19, 2017, the entire contents of which are incorporated by reference herein.

TECHNICAL FIELD

The present disclosure pertains to interventional medical systems, and more particularly to those that include relatively compact medical devices and associated tethering assemblies.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical and/or MRI compatibility issues, which are sometimes associated with elongate lead wires and well known to those skilled in the art, have motivated the development of implantable cardiac pacing devices that are wholly contained within a relatively compact package, the entirety of which is configured for implant in close proximity to the pacing site. Such devices, designed to be fully implanted in the heart, may be referred to as an intracardiac device or a leadless implantable medical device.

A delivery catheter may be used to deliver an intracardiac device transvenously to an implant site. The delivery catheter may be designed to guide the device to the appropriate implant location in the heart, allow for proper positioning of the device, and to release the device after the device has been fixed at the implant site. The delivery catheter is then removed and the device remains at the implant site.

SUMMARY

Aspects of this disclosure related to a tethering assembly, which may be part of a delivery catheter for delivering an implantable medical device to an implant site. In some examples, the tethering assembly may be part of an interventional medical system that includes a relatively compact implantable medical device (IMD) (e.g., an intracardiac device). For example, the tethering assembly may be employed by a delivery catheter configured to contain the device and deliver the device to an implant site. According to aspects of this disclosure, the tethering assembly includes an attachment component that is configured to receive an attachment member or projection of the IMD. The attachment component of the tethering assembly has a passageway and a receptacle, and a wire of the tethering assembly moves from a first position in which the wire is disposed within the passageway (e.g., thereby narrowing the passageway and preventing the attachment member of the IMD from moving through the passageway) to a second position in which the wire retracts into the receptacle and out of the passageway (e.g., thereby allowing the attachment member of the IMD to be released from the tethering assembly).

According to aspects of this disclosure, the tethering assembly is reusable in that the wire is movable from the first position to the second position and from the second position to the first position. In an example for purposes of illustration, the IMD may be secured to the tethering assembly by moving the wire to the second position (in which the wire is retracted), inserting the attachment member of the IMD into the receptacle via the passageway, and moving the wire to the second position (in which the wire extends into the passageway, thereby preventing removal of the attachment member). The IMD may then be positioned at an implant site, and the IMD may be released by moving the wire from the second position to the first position (thereby unblocking the passageway). The tethering assembly may then be reloaded by repeating the foregoing steps. In some instances, the tethering assembly may increase the ease by which an operator secures the IMD for delivery to an implant site, and may also increase the ease by which the operator releases the device from securement after the device is implanted.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIG. 2A is a plan view of an interventional medical system, according to some aspects of this disclosure.

FIG. 2B is a perspective view of an example attachment member of an IMD, according to aspects of this disclosure.

FIG. 4A is a plan view, including a partial cross-section view, of an example of an interventional medical system, according to aspects of this disclosure.

FIG. 4B is a longitudinal cross-section view of a portion of a tethering assembly included the system of FIG. 4A.

FIG. 5A is a plan view of an example of an interventional medical system including a catheter assembly, according to aspects of this disclosure.

FIG. 5B is a cross-section view through a portion of the system of FIG. 5A.

DETAILED DESCRIPTION

Figure 1A:
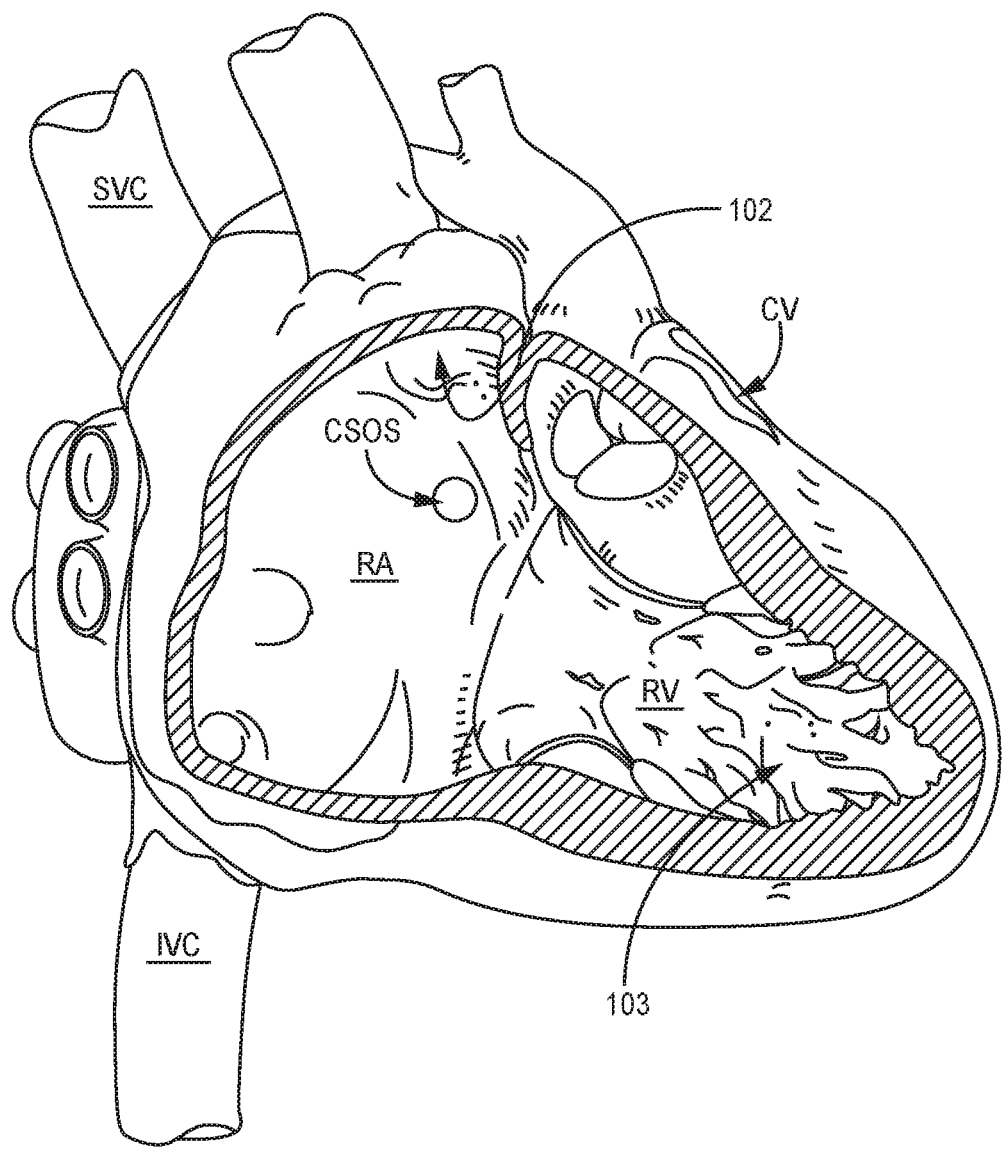
FIG. 1A is a schematic diagram showing potential implant sites for a relatively compact implantable medical device (IMD).

FIG. 1A is a schematic diagram that shows potential cardiac implant sites for an implantable medical device (IMD), e.g., an intracardiac device. Aspects of this disclosure generally relate to a tethering assembly that may be incorporated into a delivery catheter for delivering an IMD to an implant site. For example, the IMD may be secured to the tethering assembly, the delivery catheter may be guided to the implant site, and the tethering assembly may release the IMD at the implant site. In one example, the device may be implanted within an appendage 102 of a right atrium RA, within a coronary vein CV (via a coronary sinus ostium CSOS). In another example, the device may be implanted in proximity to an apex 103 of a right ventricle RV. In still other examples, the disclosed techniques may be used to implant the device in any suitable location (e.g., atrial septum or the like).

Figure 1B:
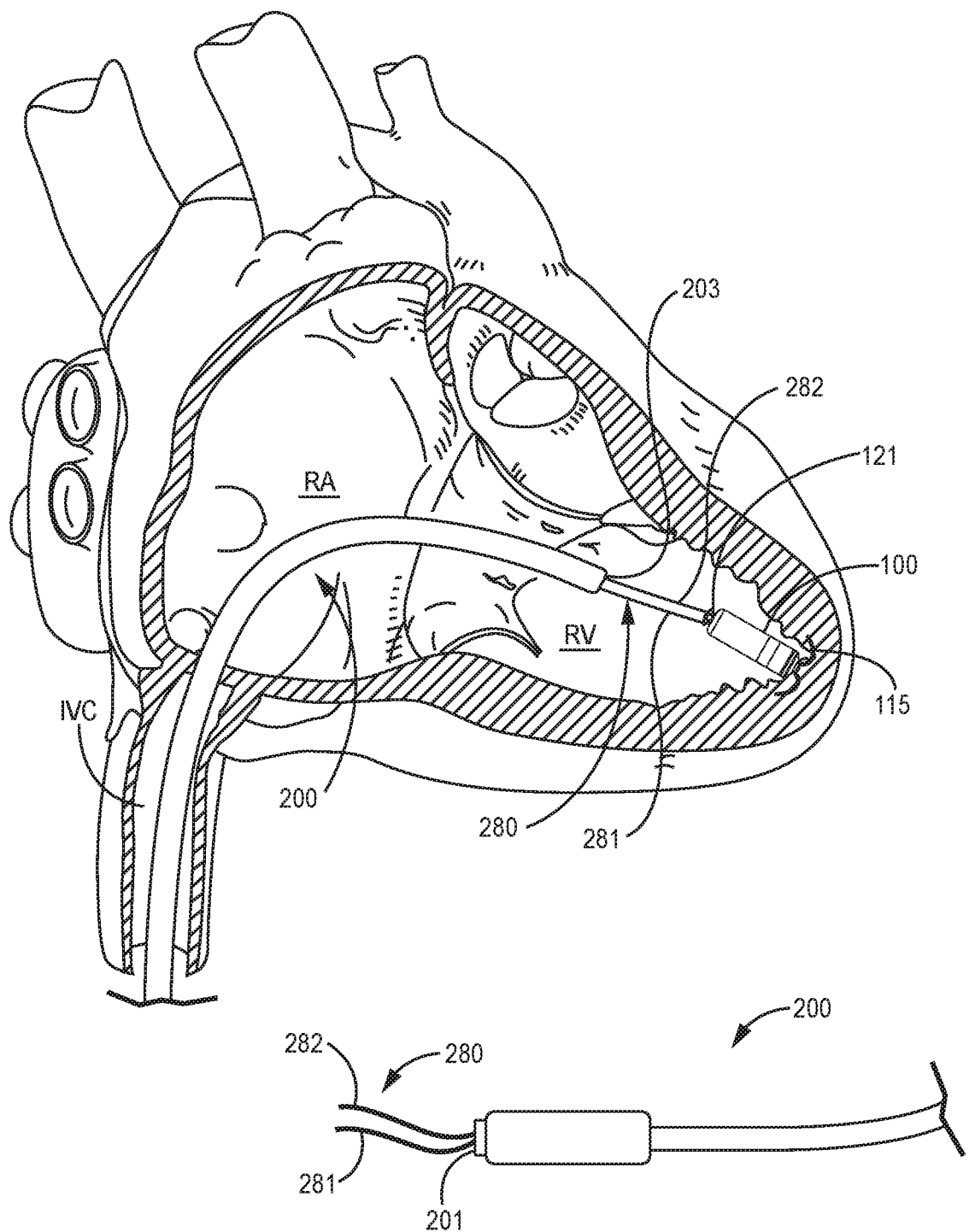
FIG. 1B is a schematic showing an exemplary relatively compact implantable medical device having been delivered from a catheter to an implant site.

FIG. 1B illustrates a relatively compact IMD 100 having been delivered through a delivery catheter 200, which an operator has maneuvered up through the inferior vena cava IVC and the right atrium RA into the right ventricle RV. IMD 100 and delivery catheter 200 may be similar to the device and tool, respectively, described in the commonly assigned U.S. Pat. No. 9,526,522, assigned to Medtronic.

In some instances, IMD 100 may be a pacemaker device having a housing that contains electronic components suitable for performing a variety of pacing functions. For example, IMD 100 may include an application specific integrated circuit (ASIC), an electronic circuit, a processor (shared, dedicated, or group) and memory that execute one or more software or firmware programs, a combinational logic circuit, state machine, or other suitable components or combinations of components that provide pacing functionality. The particular form of software, hardware and/or firmware employed to implement the functionality disclosed herein will be determined primarily by the particular system architecture employed in the pacemaker and by the particular detection and therapy delivery methodologies employed by the pacemaker.

IMD 100 is shown fixed at an implant site by a fixation member 115, but still secured to catheter 200 by a flexible tether 280 that extends out from distal opening 203 of catheter 200. Catheter 200 is joined to a holding member 121 of device 100. Thus, the operator, via tether 280, is able to test the fixation of IMD 100 at the implant site, and/or remove IMD 100 from the implant site for repositioning at a more suitable site, if necessary. While IMD 100 is shown having fixation member 115 that includes a plurality of tine structures, it should be understood that the techniques of this disclosure are not limited to any particular device fixation structure. For example, as described in greater detail herein, the disclosed devices may be used to rotate a screw-shaped fixation structure (helix) into tissue at an implant site.

Once satisfied with the implant of IMD 100, the operator can separate tether 280 from IMD 100, for example, by releasing an end of one length 281 of tether 280, and then pulling on an end of another length 282 of tether 280 to withdraw an entirety of length 282 proximally through delivery catheter 200 so that tether length 281 is pulled distally and through device holding member 121.

Securing IMD 100 to delivery catheter 200 with tether 280 is typically accomplished by looping tether 280 through device holding member 121, after which first and second lengths 281, 282 of tether 280 are threaded through one or more lumens of catheter 200. In this example, opposing ends of tether 280 protrude out from a proximal opening 201 of catheter 200 (as shown in the lower portion of FIG. 1B). In some instances, a manufacturer of device 100 and catheter 200 may secure the two together as a system, and provide the system to the operator in a single sterile package.

Aspects of this disclosure relate to a tethering assembly that, in some instances, may replace tether 280. For example, as described in greater detail herein, the tethering assembly may include an attachment component that engages and releases device holding member 121 of IMD 100 based on the position of a wire relative to an opening and passageway of the attachment component. The wire is repositionable using a release assembly at the proximal end of a delivery catheter.

Hence, according to aspects of this disclosure, an operator may couple the attachment component at the time of an implant procedure. In addition, the operator may release IMD 100 from the tethering assembly without pulling tether 280 through device holding member 121 after implant. In some instances, releasing IMD 100 using the tethering assembly described herein may reduce complications associated with other attachment mechanisms, such as tether 280 (e.g., tension associated with pulling on tether 280, potential twisting or binding of tether 280, or the like). In addition, IMD 100 may be packaged separately from the tethering assembly and delivery catheter described herein. In some instances, IMD 100 may include a drug eluting component that has a finite shelf life. In such instances, packaging the tethering assembly and delivery catheter separately from IMD 100 may mitigate shelf life considerations with respect to the tethering assembly and delivery catheter.

FIG. 2A is a plan view of an example of an interventional medical system that includes a relatively compact IMD 300 and a tethering assembly 500, while FIG. 2B is a perspective view of an example attachment member of IMD 300. In some instances, the system may further include a delivery catheter assembly (e.g., as described in greater detail below with respect to the example of FIGS. 5A-B).

In the illustrated example, device 300 includes a hermetically sealed housing 380 that extends between a proximal end 381 thereof and a distal end 382 thereof, along a longitudinal axis 3 of device 300. Housing 380 may contain a pulse generator and an associated power supply and an electrode 320, which is shown mounted to housing distal end 382 may be electrically coupled to the pulse generator via a hermetically sealed feedthrough assembly. Device housing 380 may be formed from a biocompatible and biostable metal such as titanium and may be overlaid with an insulative layer (e.g., a medical grade polyurethane, parylene, or silicone). In some instances, device 300 may include another electrode formed by removing a portion of the insulative layer to expose the metallic surface of housing 380. The other electrode may function in conjunction with electrode 320 for bipolar pacing and sensing.

Device 300 also includes shroud structure 90, which may be coupled to tethering assembly 500 for deployment of device 300 to an implant site. In the illustrated example, device projecting member 390 (also referred to herein as an attachment member of IMD 300) is joined to device housing proximal end 381 by shroud structure 90. In the illustrated example, device projecting member 390 comprises a pin (also referred to as a strut) that is welded or otherwise fixedly attached to shroud structure 90. Projecting member 390 has an elongate holding surface 395 that is spaced apart from housing proximal end 381 and that extends along a length L3, substantially orthogonal to longitudinal axis 3 of device 300.

Shroud structure 90 defines a cavity 901 with an opening 900 and projecting member holding surface 395 is exposed at opening 900. Projecting member 390 spans opening 900, for example, being welded at either end to opposing sides of shroud structure 90. It should be understood that shroud structure 390 and device projecting member 390 are provided for example only, and that a variety of other attachment members of IMD 300 are possible.

In the example illustrated in FIG. 2A, tethering assembly 500 includes an elongate shaft 510 and an elongate wire 560 that extends in sliding engagement within shaft 510. Shaft 510 is shown including a proximal portion 511, a distal portion 512 (also referred to herein as an attachment component), a retainer zone 513. While shaft 510 is described in some examples herein as including distal portion 512, the configuration of tethering assembly 500 is not limited in this way. That is distal portion 512 may be a separate component that is coupled to shaft 510 (e.g., via crimping, welding, or the like). Distal portion 512 includes receptacle 52 having a passageway 54 that provides access to receptacle 52 and that is narrower than receptacle 52.

According to aspects of this disclosure, wire 560 may extend into receptacle 52 to secure IMD 300 to tethering assembly 500 and may retract into receptacle 52 to release IMD 300 from tethering assembly 500. For example, wire 560 is moveable within shaft 510 and is repositionable between a first position in which a distal most tip of wire 560 extends into passageway 54 of receptacle 52 thereby narrowing passageway 54 and a second position in which the distal most tip retracts into receptacle 52 thereby opening passageway 54. In some examples, the distal most tip of wire 560 is displaced approximately 0.100 of an inch between the first position and the second position. Hence, device projecting member 390 may be inserted into receptacle 52 via passageway 54 when wire 560 is located in the second position. Wire 560 may then be moved to the first position, thereby blocking a portion of passageway 54 and preventing projecting member 390 from being withdrawn from receptacle 52 via passageway 54.

In this way, as described in greater detail herein, when projecting member 390 is located in receptacle 52 and wire 560 is located in the first position, application of a pulling force to IMD 300 along axis 3 and away from tethering assembly 500 results in device projecting member 390 contacting wire 560. Because wire 560 is located in passageway 54, projecting member 390 cannot move through passageway 54 until wire 560 is moved to the second position. According to aspects of this disclosure, tethering assembly 500 is reusable in that wire 560 is able to be extended into and retracted from receptacle 52 more than once. That is, the components of tethering assembly 500 remain intact after moving wire 560 from the first position to the second position and from the second position to the first position.

According to aspects of this disclosure, shaft 510 may be constructed such that shaft 510 capable of transferring torque applied at a proximal end of shaft 510 to distal portion 512 (also referred to as the attachment component). For example, shaft 510 may be composed of any combination of material and components that are of sufficient torsional rigidity such that application of rotational torque at proximal portion 511 (e.g., the relative end of proximal portion 511 opposite distal portion 512) results in rotation of distal portion 512.

In an example for purposes of illustration, shaft 510 is constructed such that application of 1 turn proximal portion 511 of shaft 510 results in 0.5-1 turn at distal portion 512 of shaft 510 for a near 1:1 torque transfer. Further, shaft 510 may be composed of a material that is sufficiently flexible along the length of shaft 510 to bend without kinking when deployed in a delivery catheter. In some examples, shaft 510 may be a hollow metal cable, e.g., such as the example described with respect to FIG. 3I below. In other examples, shaft 510 may be composed of a non-metallic material.

According to aspects of this disclosure, wire 560 may be composed of any material that provides sufficient column strength and stiffness such that displacing a proximal end results in displacement at the distal end of wire 560 in receptacle 52. In addition, wire 560 may be composed of a material that does not significantly compress under axial load (as such compression may allow wire 560 to prevent removal of projecting member 390 from receptacle 52 via passageway 54). Further, wire 560 may be composed of a material that is sufficiently flexible along the length of wire 560 to bend without kinking when deployed in a delivery catheter. In an example for purposes of illustration, wire 560 may be composed of a medical grade stainless steel or any other suitable metal alloy, such as Nitinol, MP35N (a nickel-cobalt based alloy having relatively high tensile strength), or Tantalum, although wire 560 is not required to be metallic.

In some examples, wire 560 may be sized relative to shaft 510. For example, wire 560 may have a cross-sectional dimension that is less than shaft 510, to allow longitudinal movement of wire 560 in shaft 510 along axis 3. In some examples, shaft 510 has an inside diameter of approximately 0.0095 of an inch. In some examples, wire 560 has a diameter of approximately 0.006 of an inch. In addition to allowing longitudinal movement, the difference between the cross-sectional dimension of wire 560 and the interior dimension of shaft 510 may be sized to allow for deflection of wire 560 within shaft 510 when a force is applied to the distal end of wire 560. For example, as noted above, wire 560 may be composed of a flexible material such that application of a force to distal end of wire 560 causes wire 560 to flex within shaft 510 without failing or kinking. In one example for purposes of illustration, the cross-sectional dimension of wire 560 may be approximately 0.005 of an inch (e.g., plus or minus 0.0005 of an inch), while the cross-sectional internal dimension of shaft 510 may be approximately 0.015 of an inch (plus or minus 0.001 of an inch).

By sizing wire 560 relative to shaft 510 (and having wire 560 be composed of a material that deflects without kinking or failing), wire 560 may be compressed axially as projecting member 390 moves into receptacle 52 by deflecting within shaft 510. In other examples, as described herein, an operator may manually move wire 560 from the first position to the second position (rather than wire 560 being forced between positions via projecting member 390).

In some examples, wire 560 may have a circular or ovoidal cross-sectional shape, which may allow wire 560 to rotate in shaft 510 without impacting the area of contact between wire 560 and projecting member 390 when both components are located within passageway 54. In other examples, wire 560 may be square or rectangular in shape.

According to aspects of this disclosure, shaft 510 may be coated or covered with an electrically insulating material in order to prevent electromagnetic interference with IMD 300 when coupled to IMD 300. Example coatings may include SI-Polyimide, Polyethylene terephthalate (PET), Polytetrafluoroethylene (PTFE), parylene, or a variety of other insulated coatings or tubing. Additionally, or alternatively, distal portion 512 may be constructed of or coated with an electrically insulating material.

In some examples, coatings or coverings may be applied over shaft 510 to change the flexibility and/or stiffness of shaft 510. Such coatings or coverings may be referred to herein as a stiffening component. For example, shaft 510 may have multiple components, e.g., with PET, PTFE, parylene tubing or coatings applied to at least part (or all) of shaft 510. In this example, shaft 510 may have different characteristics (such as differences in torsional rigidity) along the length of shaft 510. In an example for purposes of illustration, as noted above, shaft 510 may be composed of a hollow metal cable. In addition, a portion of the proximal portion of shaft 510 may be covered or coated in another material, such that the proximal portion of shaft 510 has a relatively high stiffness and/or torsional rigidity, while the distal end of shaft 510 that is not covered or coated may have more flexibility. In this example, the stiffening component may provide enhanced torque at proximal portion 511 without impeding flexibility of distal portion 512.

According to aspects of this disclosure, the composition of shaft 510 may be adjusted based on the characteristics of a device being delivered (such as IMD 300), the manner in which the device is delivered or fixation verified, or the implant site for the device. That is, for example, some implant sites may require shaft 510 to bend to relatively acute angles, and shaft 510 may be designed to accommodate such angles. As another example, the device may have a helical fixation element that screws into tissue at an implant site. In this example, shaft 510 may be composed of materials that have sufficient torsional rigidity to screw the helical fixation element into the tissue at the implant site.

In some instances, tethering assembly 500 may also include one or more features to prevent rotation of shaft 510. For example, proximal portion 511 may include a stop feature that prevents shaft 510 from being rotated beyond a desired rotational angle (e.g., 180 degrees), which may help to prevent tissue damage in instances in which IMD 300 is in contact with tissue during rotation. In some examples, the stop feature of proximal portion 511 may interact with a handle of tethering assembly 500. For instance, the stop feature may be a protrusion or any other feature that engages with a corresponding feature of the handle to prevent rotation of shaft 510 beyond a particular rotational angle.

FIG. 2B is a perspective view of an example attachment member of IMD 300. As noted above, shroud structure 90 may be coupled to tethering assembly 500 for deployment of device 300 to an implant site. In the illustrated example, device projecting member 390 (also referred to herein as an attachment member of IMD 300) is joined to device housing proximal end 381 by shroud structure 90. Projecting member 390 has an elongate holding surface 395 that is spaced apart from housing proximal end 381 and that extends along a length L3, substantially orthogonal to longitudinal axis 3 of device 300. Shroud structure 90 defines a cavity 901 with an opening 900 and projecting member holding surface 395 is exposed at opening 900.

According to aspects of this disclosure, distal portion 512 of tethering assembly 500 may include features that facilitate a particular interaction with a projecting member of an IMD, such as shroud structure 90 of IMD 300. For instance, in the illustrated example, distal portion 512 has a generally oblong shape that fits within the generally oblong shape of cavity 901. Hence, in instances in which shaft 510 has torsional rigidity enough to transfer torque applied at proximal end 511 to distal portion 512, rotation of shaft 510 may cause the sides of distal portion 512 to contact the sides of cavity 901, thereby causing IMD 300 to rotate. In this way, interaction between tethering assembly 500 and IMD 300 may be used to navigate and/or fixate IMD 300.

For instance, in some examples, IMD 300 may have a helical fixation element 35B that replaces fixation fingers 35 (e.g., surrounding electrode 320). In this example, helical fixation element 35B may be rotated into tissue at an implant site to fixate IMD 300 at the implant site. According to aspects of this disclosure, shaft 510 may be used to transfer torque applied at proximal end 511 to distal portion 512, thereby causing distal end to rotate 512. As noted above, distal portion 512 may interact with shroud structure 90 such that the sides of distal portion 512 to contact the sides of cavity 901, thereby causing helical fixation element 35B to be rotated into tissue at an implant site.

According to aspects of this disclosure, distal portion 512 and/or shroud 90 of IMD 300 (or any other portion of IMD 300 suitable for connection to distal portion 512) may be configured to allow or prevent a certain movement between distal portion 512 and shroud 90. For example, in some instances, distal portion 512 and shroud 90 (e.g., such as cavity 901) may be configured to allow IMD 300 to pivot with respect to shaft 510 within a particular range. In an example for purposes of illustration, cavity 901 may be sized relative to distal portion 512 (e.g., be larger than distal portion 512) to allow IMD 300 to pivot plus or minus 30 degrees vertically (opposite the direction illustrated by length L3) within cavity 901.

Figure 2C:
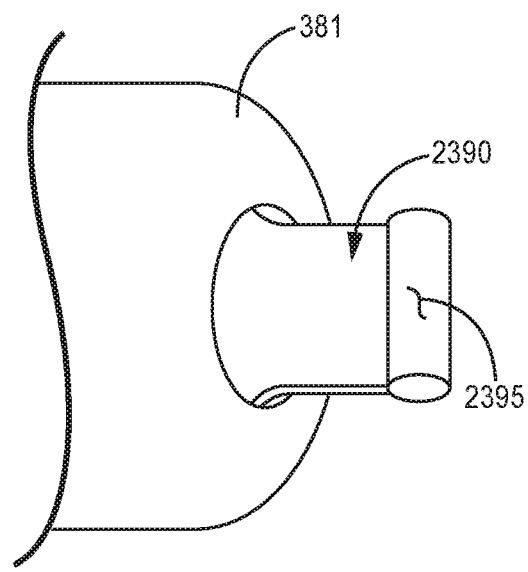
FIG. 2C is a perspective view of another example of an attachment member of an IMD.

FIG. 2C is a perspective view of another example of a projecting member 2390 (also referred to herein as an attachment member) of an implantable medical device. FIG. 2C illustrates projecting member 2390 extending proximally from proximal end 381 of device 300 to a proximal terminal end that defines a holding surface 2395 similar to holding surface 395 of projecting member 390. Projecting members 390, 2390 may be formed from medical grade stainless steel or titanium.

While distal portion 512 is generally illustrated having the same shape in the various examples described herein, it should be understood that the techniques are not limited in this way. For example, in some instances, features of distal portion 512 may be sized and shaped to be mated to a particular projecting member of an IMD, such as shroud 90 of IMD 300. Hence, while receptacle 52 of distal portion 512 is generally illustrated as having open sides, in the example of FIG. 2C, receptacle 52 may form a fully enclosed space to prevent holding surface 2395 to move laterally out of receptacle 52.

Figure 2D:
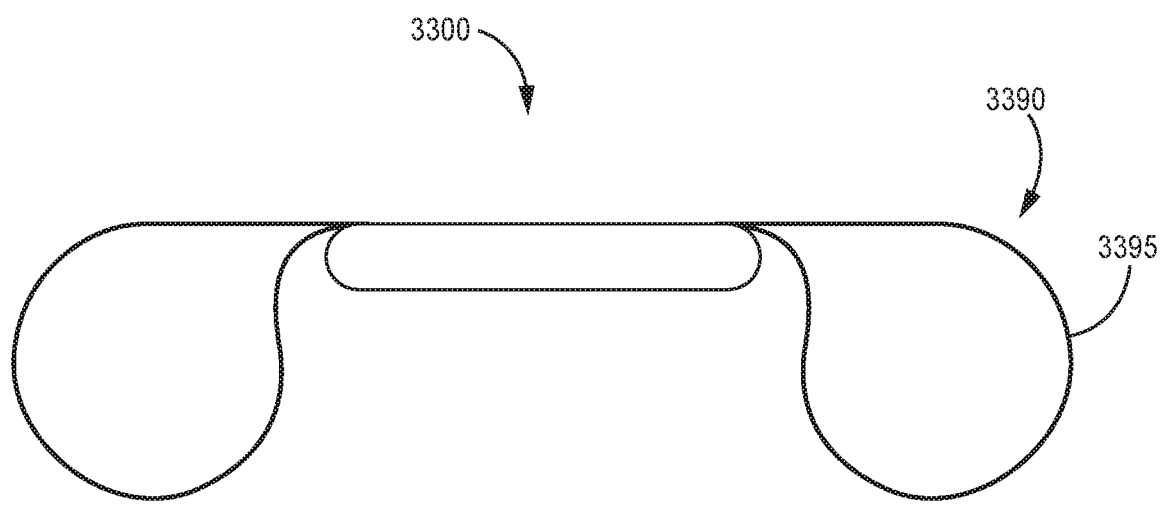
FIG. 2D is a perspective view of another example of an attachment member of an IMD.

FIG. 2D is a perspective view of another example of an implantable medical device 3300 that can be included in the system (e.g., replacing IMD 300 of FIG. 2A). In the illustrated example, device 3300 may be configured for sensing pressure, blood analytes, or other physiological properties. FIG. 2D illustrates device 3300 including a projecting member 3390 formed by a looped cable or wire that has an elongate holding surface 3395 that may be grasped and released by the tethering assemblies described herein. Any of holding surfaces 395, 2395, 3395 may have a substantially round profile or a substantially flat or square profile.

Figure 3A:
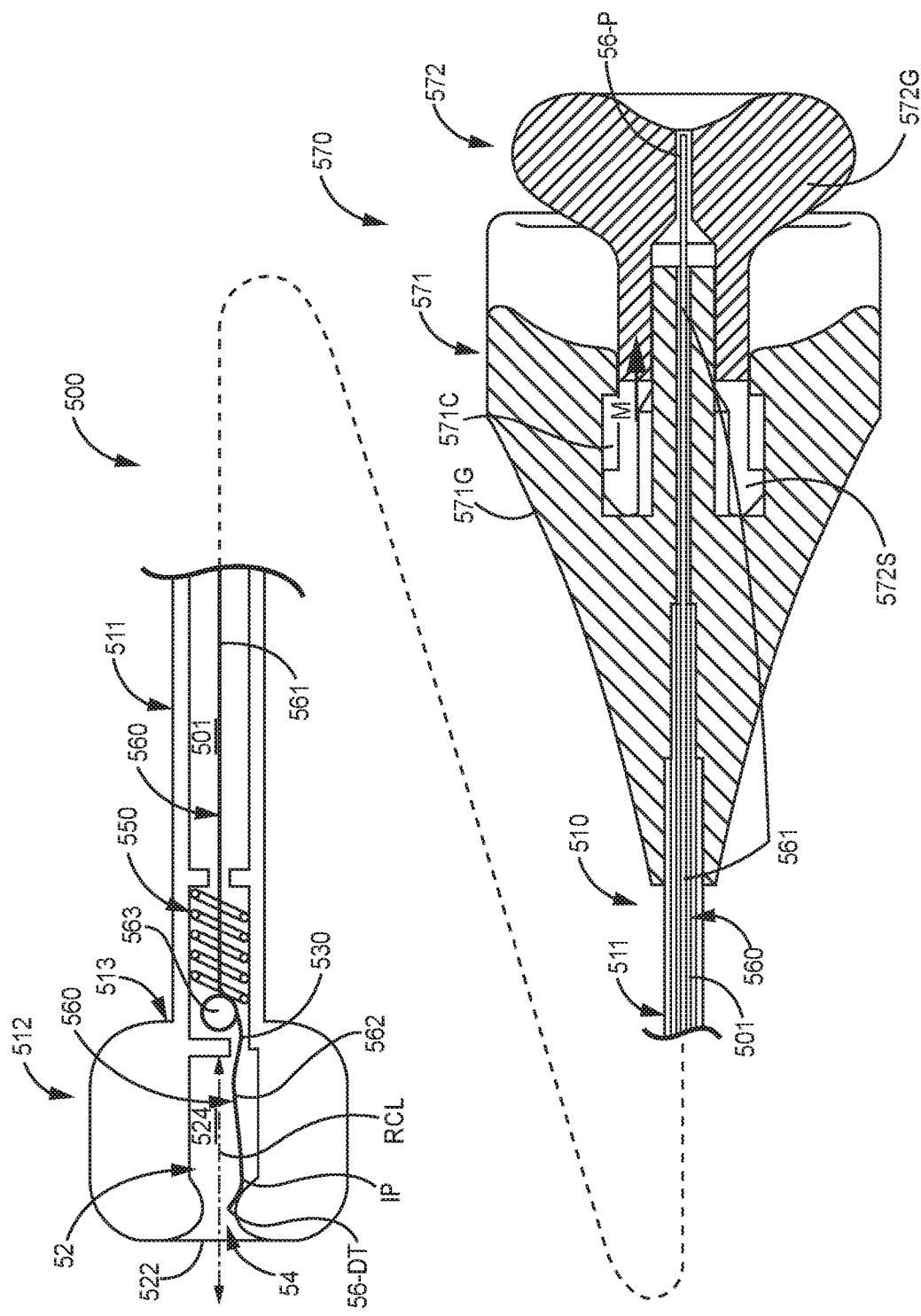
FIG. 3A is a longitudinal cross-section view of one example of a tethering assembly, according to aspects of this disclosure.

FIG. 3A is a longitudinal cross-section view of the example tethering assembly 500. It should be understood that the particular interior components and arrangement of interior components shown in FIG. 3A is provided for purposes of example only, and that other sets or subsets of components and other arrangements of such components are within the scope of this disclosure (as described, for example, with respect to the examples of FIGS. 3E-3I).

In the illustrated example, shaft proximal portion 511 includes a longitudinally extending lumen 501. Shaft distal portion 512 includes a receptacle 52 that is in communication with lumen 501, via a channel 530 of shaft retainer zone 513. Again, while distal portion 512 is described in some examples herein as being a portion of shaft 510, it should be understood that distal portion may be a separate component from shaft 510 and coupled to shaft 510, e.g., via crimping, welding, threading, or the like. Receptacle 52 is shown including a distal-most opening 522, a secure zone 524, and a passageway 54 extending from opening 522 to secure zone 524. In certain examples, passageway 54 may taper down in size, proximally from distal-most opening 522.

Wire 560 is shown including a proximal segment 561, which extends in shaft lumen 501 and a distal segment 562, which extends in shaft channel 530 and shaft receptacle 52. In some examples, wire 560 also includes a transition segment 563, for example, a loop formed in wire 560, which extends therebetween. Wire proximal segment 561 extends in lumen 501, from a proximal end 56-P thereof to transition segment 563, and wire distal segment 562 extends from transition segment 563 to a distal-most tip 56-DT of wire 560, which is shown located in receptacle passageway 54 of shaft distal portion 512.

Wire 560 extends in sliding engagement within lumen 501, channel 530, and receptacle 52 of shaft 510, so that wire distal segment 562 is moveable between a lock position (e.g., a first position) and a release position (e.g., a second position), as described herein. In some examples, shaft retainer zone 513 stops transition segment 563 of wire 560 from moving distally into receptacle 52 of shaft distal portion 512, thereby restraining wire distal-most tip 56-DT from moving through receptacle distal-most opening 522. According to the illustrated example, the profile of wire transition segment 563 is too large to move through channel 530 of retainer zone 513.

FIG. 3A further illustrates a spring member 550 extending around wire proximal portion 561 and abutting wire transition segment 563, according to some examples, to bias transition segment 563 into a confronting engagement with retainer zone 513, thereby locating distal-most tip 56-DT of wire 560 in receptacle passageway 54. Spring member 550 is shown in the form of a coil, for example, a medical grade stainless steel coil, but another example of spring member 550 may employ an elastomeric ring having suitable spring properties.

While the example shown in FIG. 3A includes both transition segment 563 and spring 550, other examples of tethering assembly 500 (e.g., such as those described below with respect to FIGS. 3E-3F and FIG. 3I) may not include one or both of transition segment 563 or spring 550. In such examples, the position of wire 560 (and distal-most tip 56-DT) may be controlled using a release assembly coupled to the proximal end of wire 560.

In any case, when wire 560 is in the illustrated spring-biased position, wire distal segment 562 is in the lock position with wire distal-most tip 56-DT extending in shaft receptacle passageway 54. Thus, device projecting member 390 confronts wire distal-most tip 56-DT, as projecting member 390 passes through distal-most opening 522 and into passageway 54, to push wire 560 proximally, against the spring-bias thereof. A size of distal-most opening 522 freely accommodates passage of device projecting member 390 (or projecting members 2390, 3390) therethrough, but the tapered-down size of passageway 54 only accommodates passage of projecting member 390 (2390, 3390) therethrough and into secure zone 524 when distal segment 562 of wire 560 does not extend into passageway 54.

In some examples, such as that shown in FIG. 3A, wire distal segment 562 has a pre-formed curvature such that distal segment 562 extends away from a longitudinal center-line RCL of shaft receptacle 52 between wire transition segment 563 and an inflection point IP of distal segment 562, and extends toward center-line RCL between inflection point IP and wire distal-most tip 56-DT. Again, while the example of FIG. 3A illustrates wire 560 having a pre-formed curvature, other examples may not include such a curvature (e.g., such as the examples described with respect to FIGS. 3E, 3G, 3H, and 3I below, in which distal segment 562 of wire 560 is substantially straight).

Figure 3B:
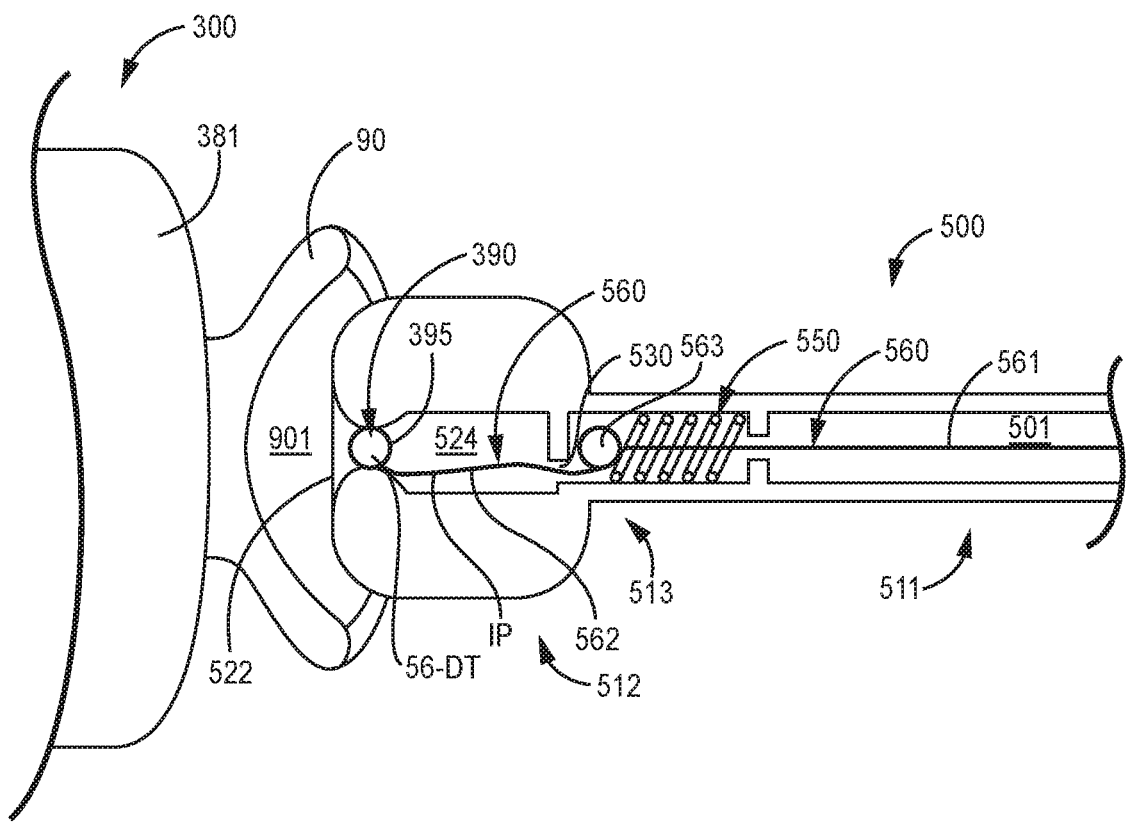
FIG. 3B is a longitudinal cross-section view of an example of a tethering assembly, according to aspects of this disclosure.

FIG. 3B illustrates projecting member 390 moving proximally (relative to the example of FIG. 3A) and pushes wire distal-most tip 56-DT into secure zone 524 of shaft receptacle 52. As a longitudinal force is applied, holding surface 395 of projecting member 390 is allowed to pass into secure zone 524.

FIG. 3B illustrates holding surface 395 of device projecting member 390 entering secure zone 524. Here, wire distal-most tip 56-DT moves, according to the bias of the spring member 550, distally, alongside projecting member 390 and back into passageway 54, to the lock position of distal segment 562. Holding surface 395 of projecting member 390 seats against wire distal segment 562, in proximity to inflection point IP thereof. The protrusion of wire distal-most tip 56-DT into passageway 54 (lock position), distal to device projecting member holding surface 395, blocks passageway 54 and creates a mechanical interlock with projecting member 390 to secure device 300 to tethering assembly 500. That is, applying force to IMD 300 away from tethering assembly 500 results in contact between wire distal segment 562 and projecting member 390 and passageway 54 is narrowed in a manner that does not allow projecting member 390 to pass through.

To release device 300 from tethering assembly 500, proximal end 56-P of wire 560 (FIGS. 2A, 3A) may be engaged to move wire distal segment 562 proximally, relative to shaft 510 and device 300, into the aforementioned release position, at which wire distal-most tip 56-DT is retracted past projecting member holding surface 395 within secure zone 524, so that tip 56-DT no longer blocks passageway 54.

With further reference to FIG. 3A, a handle 570 (also referred to herein as a release assembly) of tethering assembly 500 includes a first part 571 and a second part 572, wherein first part 571 is shown coupled to shaft proximal portion 511, and second part is shown coupled to wire proximal end 56-P. Each part 571, 572 of handle 570 is shown having a grip region 571G, 572G to facilitate handling for the operation of tethering assembly 500. FIG. 3A further illustrates a shank 572S of handle second part 572 interlocking in a cavity 571C of handle first part 571.

In the illustrated example, the interlocking engagement between first and second parts 571, 572 allows for a limited longitudinal movement of second part 572 relative to first part 571 between a first position and a second position, the first position being shown in FIG. 3A and corresponding to the lock position of wire distal segment 562. Movement of handle second part 572, per arrow M, to the second position, moves wire 560 proximally relative to shaft 510 to bring wire distal segment 562 into the aforementioned release position. Other examples of release assemblies are described below in conjunction with FIGS. 5A and 6.

Figure 3C:
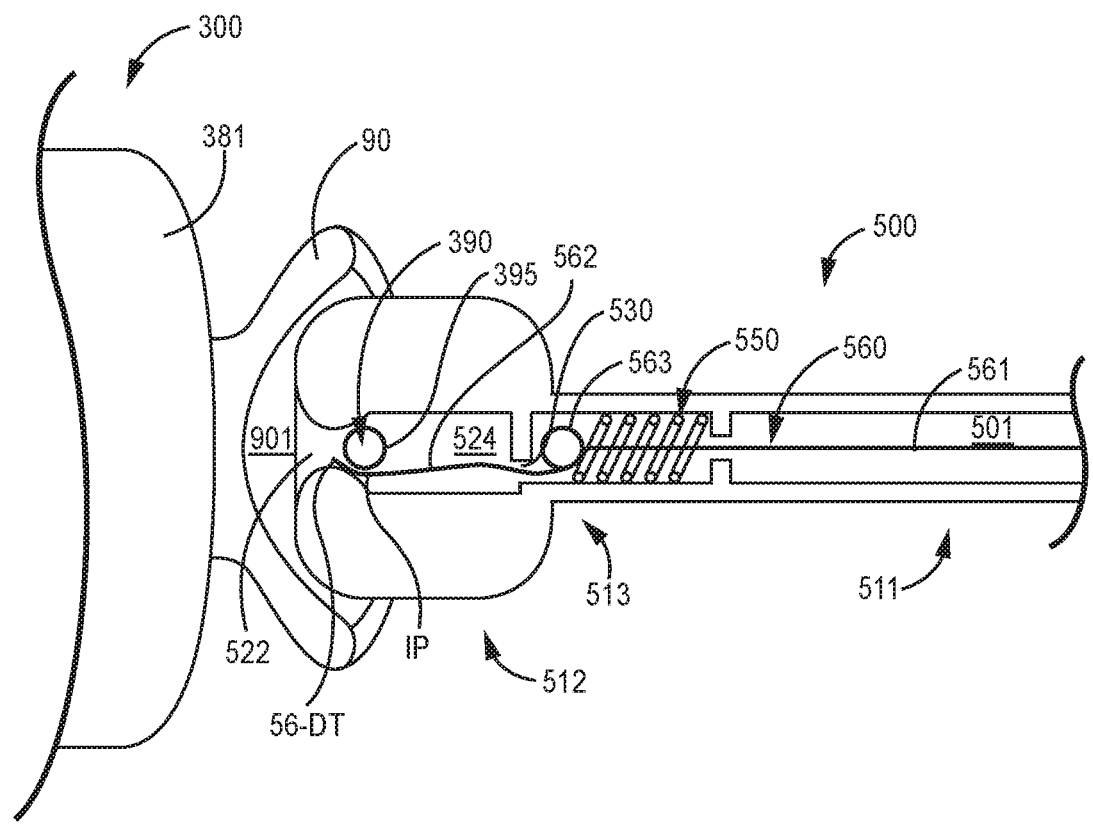
FIG. 3C is another longitudinal cross-section view of an example of a tethering assembly, according to aspects of this disclosure.
Figure 3D:
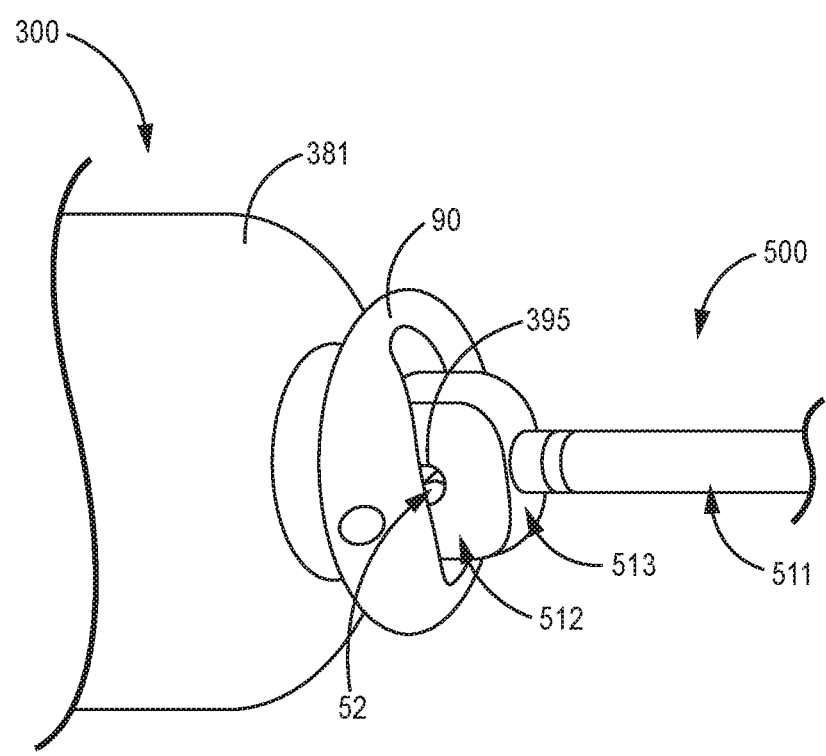
FIG. 3D is a perspective view of the example tethering assembly shown in FIG. 3C.

FIG. 3D is a perspective view of device 300 secured to tethering assembly 500. With reference back to FIG. 2A, in conjunction with FIG. 3D, it can be seen that, in some examples, a sidewall of shaft distal segment 512 does not extend all the way around a lateral perimeter of receptacle 52. In such examples, receptacle 52 is formed as an open-sided slot in shaft distal segment 512. Such a configuration of distal segment 512 provides clearance for shroud structure 90 as device projecting member 390 moves through receptacle opening 522 and passageway 54 and into receptacle secure zone 524. In other examples, the sidewall of the distal segment of the tethering assembly shaft can extend all the way around the lateral perimeter of the receptacle thereof, since such clearance is not necessary for alternative projecting member configurations.

As noted above, in some examples, shaft 510 may be constructed in a manner that allows rotational torque applied at shaft proximal end 511 to be transferred to distal portion 512. In such examples, the rotational torque may be used to rotate IMD 300 when distal portion 512 is coupled to projecting member 390. For example, rotation of distal portion 512 (via rotation of shaft 510) may further cause rotation of IMD 300 due to IMD 300 being coupled to distal portion 512.

FIGS. 3E-3I illustrate additional examples of tethering assembly 500. In the illustrated examples, tethering assembly 500 is shown in cross-section views with device projecting member 390 located in receptacle passageway 54 of shaft distal segment 512 and confronting wire distal-most tip 56-DT. Again, it should be understood that the particular interior components and arrangement of interior components shown in FIGS. 3E-3I are provided for purposes of example only, and that other sets or subsets of components and other arrangements of such components are within the scope of this disclosure.

Figure 3E:
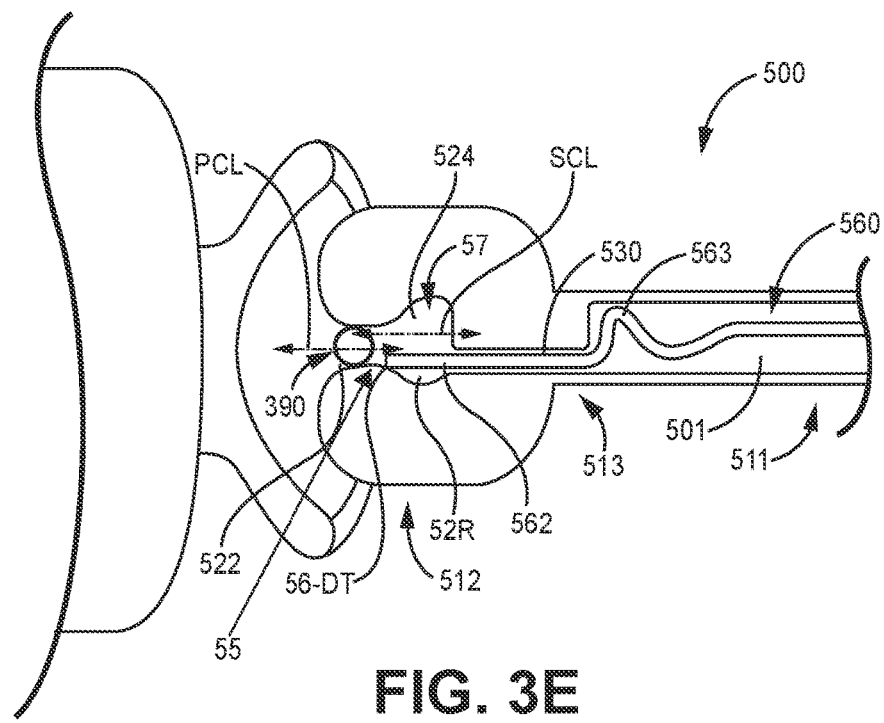
FIG. 3E is a cross-section view of an example tethering assembly and IMD, according to aspects of this disclosure.

FIG. 3E illustrates a first example in which channel 530 of shaft retainer zone 513 is lengthened to provide additional support to wire distal segment 562, for example, to prevent buckling thereof as device projecting member 390 moves through passageway 54 of shaft distal segment 512 and confronts wire distal-most tip 56-DT to push wire 560 proximally. FIG. 3E further illustrates an example of a contour of secure zone 524, where a centerline SCL of secure zone 524 is laterally offset from a centerline PCL of passageway 54, which is also laterally offset from the longitudinal extent of wire distal segment 562.

According to aspects of this disclosure, the contour of secure zone 524 (encompassed by receptacle 52) includes offset 57. Offset 57 may provide an area into which projecting member 390 may travel to move out of the path of wire distal-most tip 56-DT when wire distal-most tip 56-DT is moving from the second position to the first position (lock position). That is, for example, the contour of offset 57 is such that receptacle 52 increases in size from a distal end of receptacle 52 nearer passageway 54 to a proximal end of receptacle 52 nearer shaft 510. In this manner, offset 57 able to accommodate horizontal and vertical movement of projecting member 390 as projecting member 390 is inserted into and moves through receptacle 52 from the distal end of receptacle 52 to the proximal end of receptacle 52.

In some examples, the contour of secure zone 524 may also include relief 52R. In such examples, relief 52R may allow some deflection of wire distal segment 562 away from secure zone centerline SCL as projecting member 390 enters secure zone 524. Such deflection may facilitate a smoother passage of projecting member 390.

In some examples, secure zone 524 and/or passageway 54 may also include a groove 55 into which at least a portion of wire 560 is disposed. For example, secure zone 524 and/or passageway 54 may include a groove 55 at the base of secure zone 524 and/or passageway 54 (e.g., the relative bottom of secure zone 524 and/or passageway 54 where relieve 52R is located). Groove 55 may have a depth that is less than the thickness of wire 560, such that wire still narrows passageway 54 when located in the first position. Groove 55 may prevent lateral movement of wire 560 in receptacle 52 as projecting member 390 is inserted into receptacle 52.

Figure 3F:
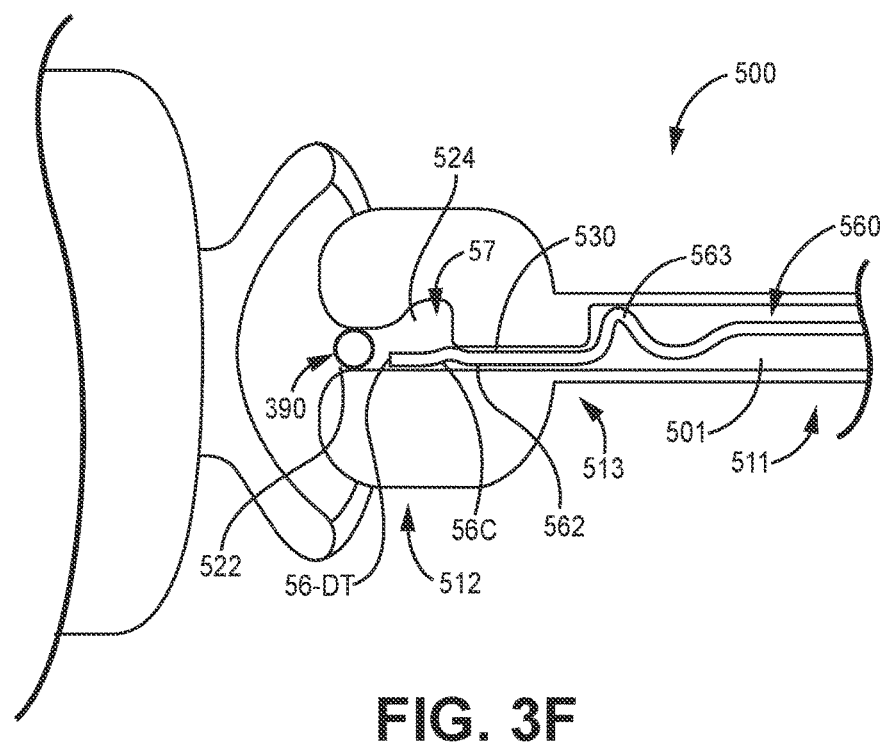
FIG. 3F is a cross-section view of another example tethering assembly and IMD, according to aspects of this disclosure.

FIG. 3F illustrates secure zone 524 having offset 57, but does not include the relief for wire distal segment 562. Rather, wire distal segment 562 is shown having a curvature 56C formed therein in proximity to distal-most tip 56-DT, for example, to facilitate smooth passage of projecting member 390 into secure zone 524.

With further reference to FIGS. 3E-F, transition segment 563 of wire 560 is shown having a sigmoidal form as one example of how wire 560 may be configured with a spring-bias so that the above described spring member 550 is not necessary. The sigmoidal form of also enlarges a profile of wire 560 so that transition segment 563 is stopped by shaft retainer zone 513 as described above.

Figure 3G:
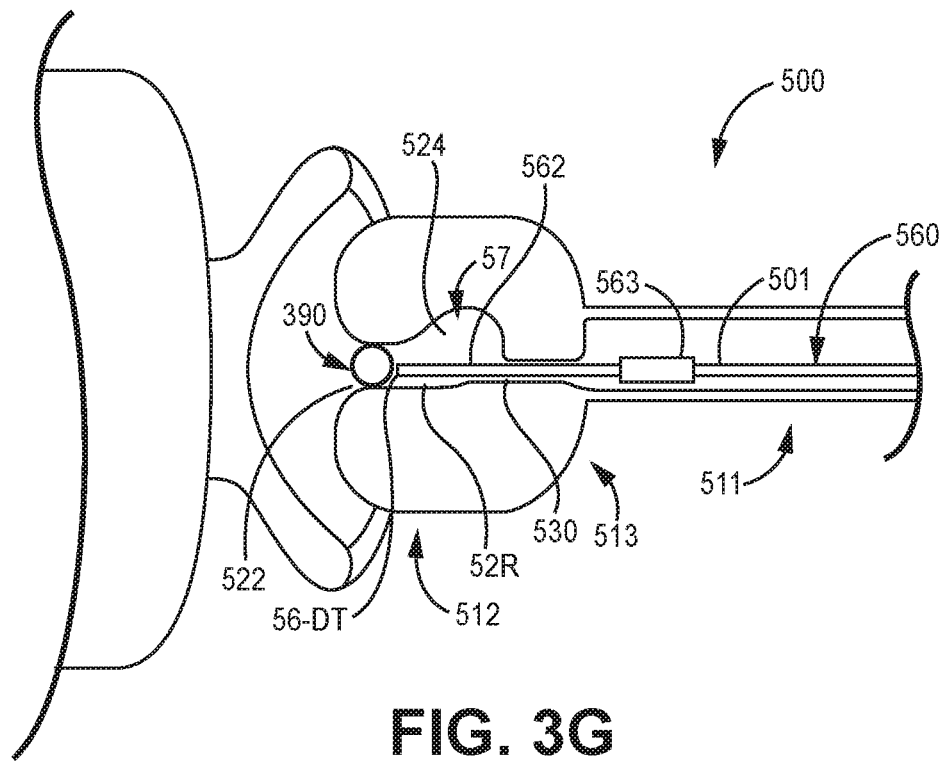
FIG. 3G is a cross-section view of another example tethering assembly and IMD, according to aspects of this disclosure.

FIG. 3G illustrates another example in which secure zone 524 is similarly offset and includes relief 52R, but the contour thereof slightly differs from that in FIG. 3E. According to the example shown in FIG. 3G, transition segment 563 of wire 560 is enlarged in diameter, for example, by having a sleeve mounted thereabout.

Figure 3H:
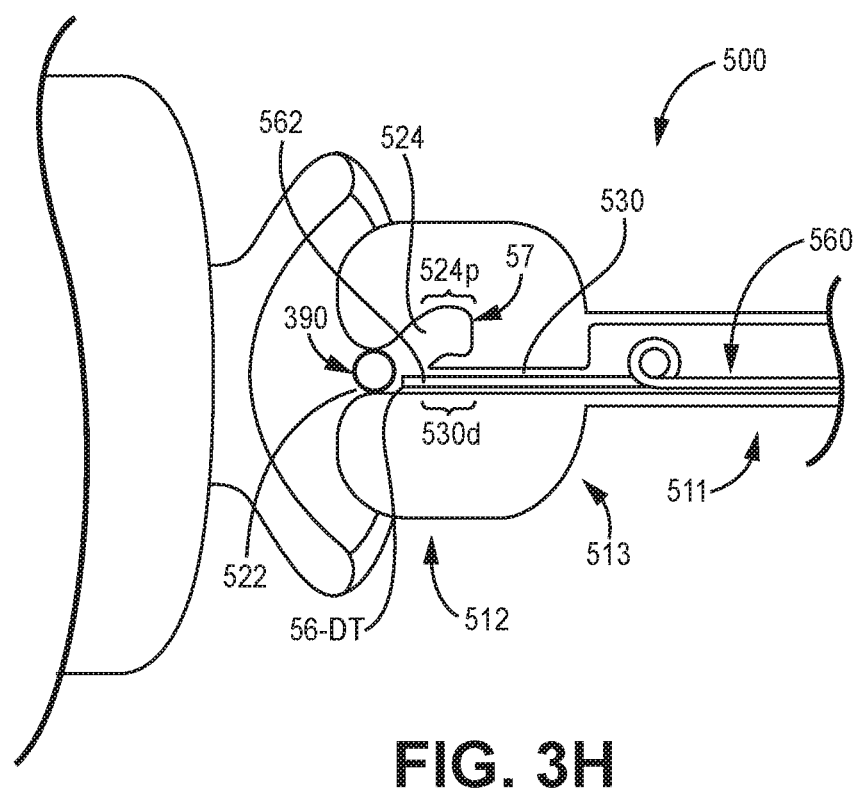
FIG. 3H is a cross-section view of another example tethering assembly and IMD, according to aspects of this disclosure.

FIG. 3H illustrates yet another contour for secure zone 524 of shaft distal segment 512. In FIG. 3H, secure zone 524 is shown being laterally offset from passageway 54 and including a proximal portion 524p that extends longitudinally alongside a distal portion 530d of retainer zone channel 530. For example, proximal portion 524p is an example of a projection that is positioned at the base of offset 57 and that extends into receptacle 52 from the proximal end of receptacle 52. In some examples, proximal portion 524p is a projection that is shaped to divert projecting member 390 of IMD 300 into offset 57 as projecting member 390 is inserted into receptacle 52 from the distal end of receptacle 52.

Figure 3I:
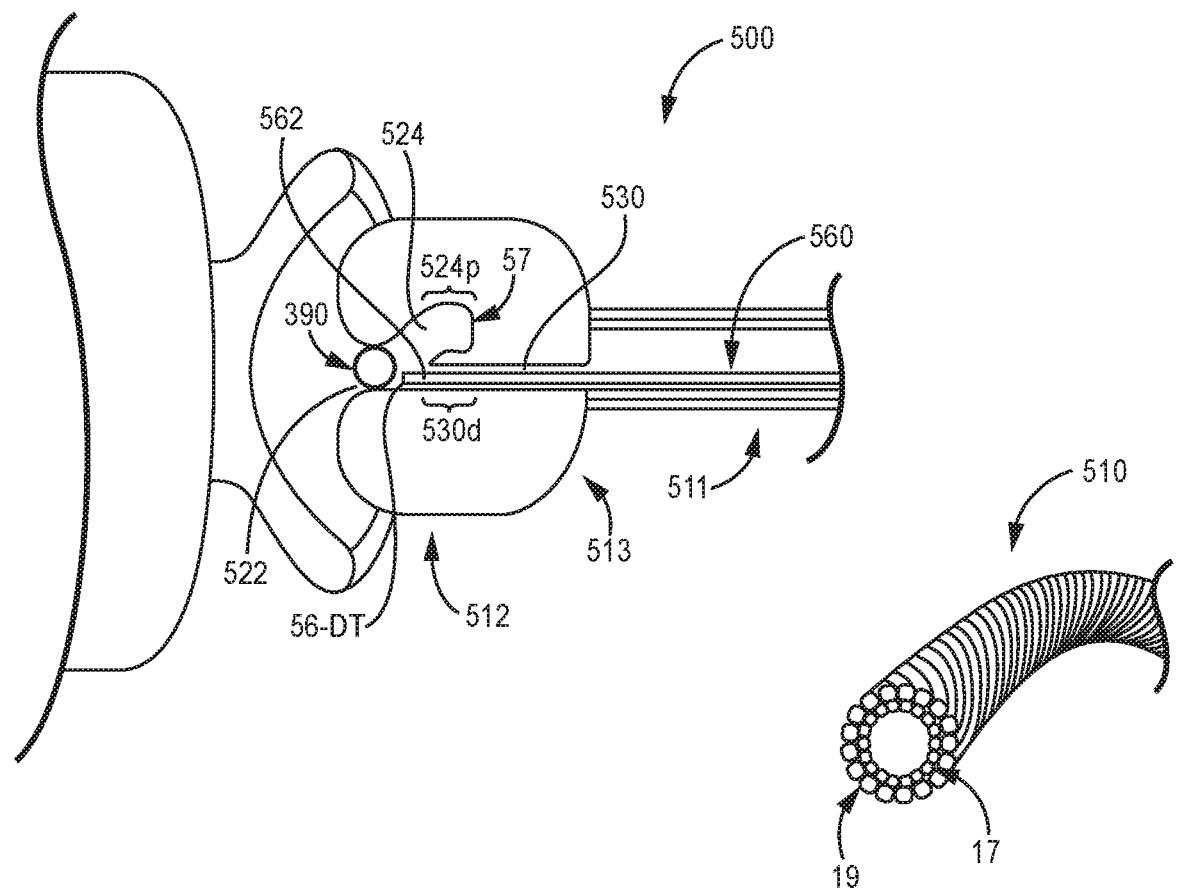
FIG. 3I is a cross-section view of another example tethering assembly and IMD, according to aspects of this disclosure.

FIG. 3I is another example of tethering assembly 500 having offset 57 and proximal portion 524p. In the example of FIG. 3I, wire 560 does not include spring member 550 or transition segment 563. In this example, wire 560 may be biased via a handle or release assembly coupled to proximal portion 511 of wire 560.

FIG. 3I also illustrates one example of a composition of shaft 510. In the illustrated example, shaft 510 is a hollow stranded cable that includes an interior component 17 and an outer component 19. In some examples, a hollow stranded cable is a coiled cable composed of a number of filars that are wrapped together. The filars may be compressed such that the filars remain in close contact. One example of a hollow stranded cable shown in FIG. 3I is the Helical Hollow Strand® tube manufactured and sold by Fort Wayne Metals Co. In other examples, a hollow stranded cable may be composed of braided filars. In one example, shaft 510 is a hollow stranded cable with interior component 17 having an interior diameter of approximately 0.014 of an inch in diameter (plus or minus 0.003 of an inch).

In some examples, interior component 17 and outer component 19 may have a pitch and filar count that allow torque applied at one end of shaft 510 to be transferred to the other end of shaft 510. In some instances, interior component 17 and outer component 19 may be bidirectional, in that the direction of the pitch of interior component 17 runs opposite of the direction of the pitch of outer component 19.

According to aspects of this disclosure, the composition of shaft 510 has tensile properties resulting in relatively low elongation along the length of shaft 510. As such, the position of wire 560 may be adjusted with a relatively high precision with respect to shaft 510. That is, the working dimensions of shaft 510 are static, such that the correspondence between the position of wire 560 and the position of shaft 510 remains relatively constant.

As noted above, rotational torque may be used to rotate IMD 300 when distal portion 512 is coupled to projecting member 390. That is, an operator may apply rotational torque to proximal portion 511 of wire 560 (e.g., via a handle or release assembly), which may cause rotation of distal portion 512 (via rotation of shaft 510). Such rotation may further cause rotation of IMD 300 due to IMD 300 being coupled to distal portion 512.

The actual torque transfer between the proximal portion 511 and the distal portion 512 of shaft 510 may be a function of a variety of factors. For example, the torque transferred between proximal portion 511 and distal portion 512 may be a factor of a length of shaft 510, the component makeup of shaft 510 (e.g., whether shaft 510 is coated or covered with materials that stiffen shaft 510), the resistance of material/tissue surrounding IMD 300 (and the fixation component of IMD 300) at an implant site, or the like. In an example for purposes of illustration, an approximately 50-inch-long tethering assembly 500 having a stranded cable shaft (such as that shown in FIG. 3I) with a 0.002 of an inch-thick PET heat shrink may have a torque transfer (build up) of approximately 0.52 inch-oz for one clockwise turn of the proximal portion 511 when the distal portion 512 is held fixed. Due to the characteristics of the braid, the torque in the counter clockwise direction may be less, e.g., approximately half.

Figure 3J:
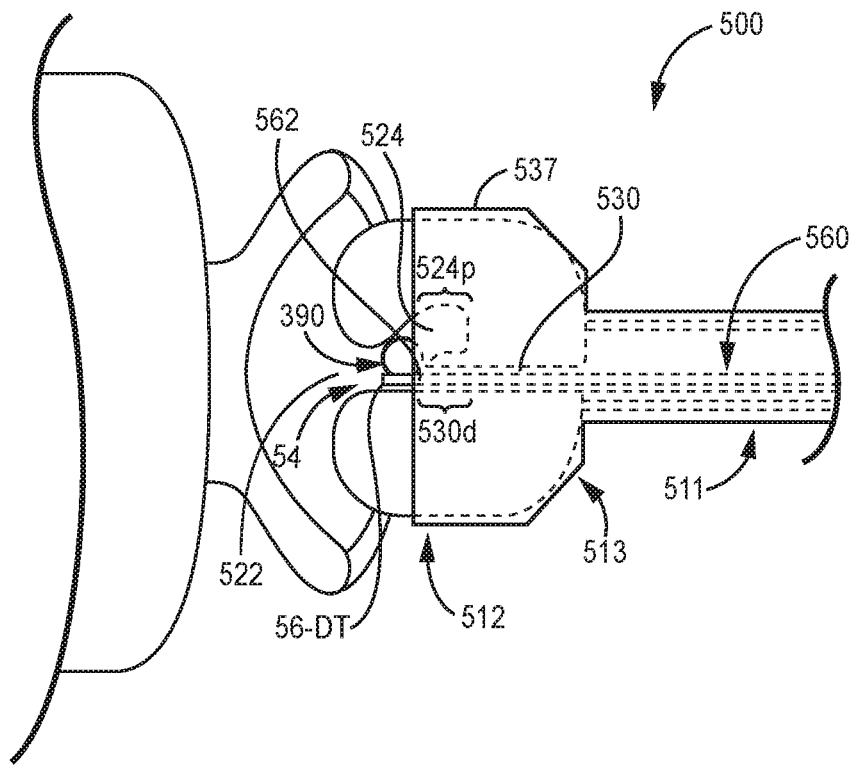
FIG. 3J is a cross-section view of another example tethering assembly and IMD, according to aspects of this disclosure.

FIG. 3J is another example of tethering assembly 500 (such as the example shown in FIG. 3I having offset 57 and proximal portion 524p). The example of FIG. 3J illustrates device projecting member 390 as being located in secure zone 524 and with distal-most tip 56-DT moved into the first position (lock position). Accordingly, as described herein, the width of distal-most opening 522 is sufficiently narrowed by wire 560 that device projecting member 390 cannot be removed from secure zone 524, at least without removing or deforming wire 560. It should be understood that the example shown in FIG. 3J is provided for purposes of illustration only, and that distal-most tip 56-DT may be further extended or retracted in the first position (lock position).

The example shown in FIG. 3J includes a sleeve 537. In the illustrated example, sleeve 537 is a component that is positioned over the exterior surface of distal portion 512 and that covers at least a portion of distal portion 512. Sleeve 537 may be composed of silicone or a variety of other polymers or substances. In some instances, sleeve 537 may be flexible in that at least a portion of sleeve 537 may deform (e.g., around device projecting member 390, as described in greater detail below) without movement of the remaining portion of sleeve 537. In other examples, sleeve 537 may be relatively rigid. In some instances, sleeve 537 may be non-conductive and/or electrically isolated from distal portion 512 and/or device projecting member 390. In the illustrated example, sleeve 537 extends along shaft proximal portion 511. In other examples, sleeve 537 may only cover some or all of distal portion 512.

According to aspects of this disclosure, sleeve 537 may act as a biasing member that provides a force for maintaining contact between device projecting member 390 and at least one surface of distal portion 512. For example, sleeve 537 may be positioned and/or composed of a suitable material such that sleeve 537 biases device projecting member 390 toward distal-most opening 522 and away from channel 530. That is, as device projecting member 390 is inserted into distal-most opening 522, device projecting member 390 may contact sleeve 537. Sleeve 537 may provide a resistive force against device projecting member 390 that is directed toward distal-most opening 522, but that still allows device projecting member 390 to move into secure zone 524 and proximal portion 524p.

After device projecting member 390 has moved into secure zone 524 and wire distal-most tip 56-DT has moved into the first position (lock position), as shown in FIG. 3J, sleeve 537 continues to contact device projecting member 390 and biases device projecting member 390 toward distal-most opening 522. In this way, sleeve 537 provides a biasing force such that device projecting member 390 maintains contact with a surface of secure zone 524.

According to aspects of this disclosure, sleeve 537 may be configured to control the freedom of movement of device 300 when coupled to tethering assembly 500 based on a holding force (e.g., an amount of resistive force applied to device projecting member 390 to bias device projecting member 390 into maintaining contact with a surface of secure zone 524). For example, increasing the holding force may limit the freedom of movement by deice 300 after insertion of device holding member 390. Likewise, decreasing the holding force may increase the freedom of movement by deice 300 after insertion of device holding member 390. Increasing or decreasing the freedom of movement of device 300 may impact, for example, implantation procedure. For example, a relatively high holding force may allow device 300 and tethering assembly 500 to maintain a linear alignment during implantation of device 300.

The selection of material for sleeve 537 and/or the position of sleeve 537 relative to distal-most opening 522 may be based on the desired holding force. In some examples, positioning sleeve 537 further toward distal-most opening 522 (and/or selecting a relatively rigid material) may result in a relatively large holding force. That is, positioning sleeve 537 further toward distal-most opening 522 (and/or selecting a relatively rigid material) may result in a relatively large amount of force pressing device holding member 390 against a surface of secure zone 524. Alternatively, positioning sleeve 537 further away from distal-most opening 522 (and/or selecting a relatively flexible material) may result in a relatively small holding force. That is, positioning sleeve 537 further away from distal-most opening 522 (and/or selecting a relatively flexible material) may result in a relatively small amount of force pressing device holding member 390 against a surface of secure zone 524.

According to aspects of this disclosure, sleeve 537 may be configured to reduce potential electrical noise between device projecting member 390 and tethering assembly 500. For example, in some instances, secure zone 524 may be sized to be larger than device projecting member 390, such that device projecting member 390 may move within secure zone 524, thereby making and breaking contact between device projecting member 390 and a surface of secure zone 524. Such make-and-break contact may result in electrical noise, e.g., as measured by an electrode of device 300. As described herein, sleeve 537 may be configured such that device projecting member 390 maintains contact with a surface of secure zone 524, thereby reducing or eliminating make-and-break contact between device projecting member 390 and a surface of secure zone 524.

In some examples, sleeve 537 may also be configured to allow system 500 to be an electrical conduit to a device coupled to system 500, such as device 300. For example, in some instances, as described herein, shaft 510, wire 560, and/or distal portion 512 may be metallic or another electrically conductive material. By maintaining contact between electrically conductors (e.g., between device 300 and shaft 510, wire 560, and/or distal portion 512), at least a portion of assembly 500 may provide an electrical conduit from the proximal end to the distal end. Accordingly, impedance or another electrical property may be measured at the proximal end via the conduit.

Additionally or alternatively, according to aspects of this disclosure, sleeve 537 may be configured to provide electrical isolation for tethering assembly 500. For example, in some instances, one or more components of tethering assembly 500 may be electrical conductors. As noted above, sleeve 537 may be composed of silicone or another non-conductive material, thereby electrically isolating the conductive components of tethering assembly 500 from other conductors.

Figure 3K:
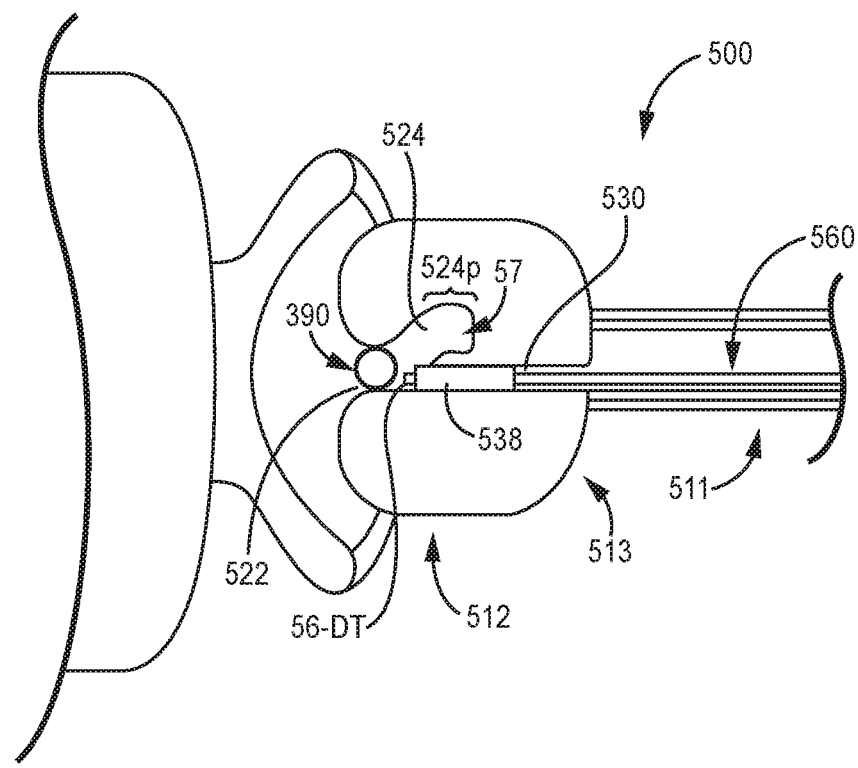
FIG. 3K is a cross-section view of another example tethering assembly and IMD, according to aspects of this disclosure.

FIG. 3K is a cross-section view of another example tethering assembly and IMD, according to aspects of this disclosure. (such as the example shown in FIG. 3I having offset 57 and proximal portion 524p) that includes a plug 538. In the illustrated example, plug 538 is a component that is positioned within channel 530 and extends at least partially into secure zone 524. In other examples, however, plug 538 may be positioned in a different position, e.g., at least partially within offset 57, provided plug 538 still functions as a biasing member that provides a force for maintaining contact between device projecting member 390 and at least one surface of distal portion 512

Similar to sleeve 537, plug 538 may be composed of silicone or a variety of other polymers or substances. In some instances, plug 538 may be flexible in that at least a portion of plug 538 may deform (e.g., around device projecting member 390). In other examples, plug 538 may be relatively rigid. It should be understood that the particular configuration of plug 538 illustrated in FIG. 3I is provided for purposes of example, and that plug 538 may extend further into secure zone 524 than shown, not as far into channel 530 than shown, or the like.

According to aspects of this disclosure, plug 538 may act as a biasing member that provides a force for maintaining contact between device projecting member 390 and at least one surface of distal portion 512. For example, plug 538 may be positioned and/or composed of a suitable material such that plug 538 biases device projecting member 390 toward distal-most opening 522 and away from channel 530. That is, as device projecting member 390 is inserted into distal-most opening 522, device projecting member 390 may contact plug 538. Plug 538 may provide a resistive force against device projecting member 390 that is directed toward distal-most opening 522, but that still allows device projecting member 390 to move into secure zone 524 and proximal portion 524p.

After device projecting member 390 has moved into secure zone 524 and wire distal-most tip 56-DT has moved into the first position (lock position), plug 538 continues to contact device projecting member 390 and biases device projecting member 390 toward distal-most opening 522. In this way, sleeve 537 provides a biasing force such that device projecting member 390 maintains contact with a surface of secure zone 524.

According to aspects of this disclosure, similar to sleeve 537 described above, plug 538 may be configured to control the freedom of movement of device 300 when coupled to tethering assembly 500 based on a holding force (e.g., an amount of resistive force applied to device projecting member 390 to bias device projecting member 390 into maintaining contact with a surface of secure zone 524). The selection of material for plug 538 and/or the position of plug 538 relative to distal-most opening 522 may be based on the desired holding force. In some examples, positioning plug 538 further toward distal-most opening 522 (and/or selecting a relatively rigid material) may result in a relatively large holding force. Alternatively, positioning plug 538 further away from distal-most opening 522 (and/or selecting a relatively flexible material) may result in a relatively small holding force.

According to aspects of this disclosure, plug 538 may be configured to reduce potential electrical noise between device projecting member 390 and tethering assembly 500. For example, plug 538 may be configured such that device projecting member 390 maintains contact with a surface of secure zone 524, thereby reducing or eliminating make-and-break contact between device projecting member 390 and a surface of secure zone 524.

In addition, in some instances, plug 538 may be configured to prevent fluid from traveling into channel 530. For example, by being positioned at the relative end of channel 530, plug 538 may prevent fluid from an implant site from entering channel during an implant procedure.

FIG. 4A illustrates a relatively compact implantable medical device 400 that includes a projecting member 490 having an alternative orientation to that of device projecting member 390. FIG. 4A is a plan view of the system, which includes a partial cross-section view through shroud 90 of device 400 so that projecting member 490 can be seen extending in cavity 901 thereof (Note that a remainder of device 400 may be the same as device 300.) The system of FIG. 4A includes a tethering assembly 600, which may be similar to tethering assembly 500 in many respects, but an elongate shaft 610 of assembly 600 has a distal portion 612 that is configured to accommodate the alternative orientation of device projecting member 490. (Note that assembly 600 is shown including elongate wire 560 and shaft proximal portion 511 as described above for assembly 500 in conjunction with FIGS. 3A-C, and may alternately employ any of the alternate configurations of wire 560 described in conjunction with FIGS. 3E-I)

FIG. 4A illustrates a length L4 of projecting member 490 extending approximately perpendicular to a plane of cavity opening 900, wherein a proximal terminal end of projecting member 490 is defined by a protuberance 495, for example, a generally spherical tip, that is spaced apart from device housing proximal end 381 and terminates length L4 in proximity to cavity opening 900. FIG. 4A further illustrates device 400 positioned so that projecting member protuberance 495 is located in proximity to a distal-most opening 622 of a receptacle 62 of shaft distal portion 612, which is shown in the longitudinal cross-section view of FIG. 4B. Like receptacle 52 of tethering assembly 500, receptacle 62 of tethering assembly 600 is in communication with lumen 501 of shaft proximal portion 511, but a sidewall of shaft distal portion 612 extends completely around center-line RCL6, and an external profile of shaft distal portion 612 may be approximately isodiametric with that of shaft proximal portion 511. Hence, whereas the example shown in FIG. 2A may allow distal portion 512 of shaft 510 to apply torque to rotate IMD 300, in the example of FIG. 4A, distal portion 512 may rotate freely around projecting member protuberance 495.

FIG. 4B illustrates shaft receptacle 62 including a passageway 623 extending proximally from distal-most opening 622 to a secure zone 624 of receptacle 62, wherein passageway 623 tapers down in size, for example, from a first diameter d1 at distal-most opening 622, to a second, smaller diameter d2 in proximity to secure zone 624, and wherein secure zone 624 has an enlarged size from passageway 623, for example, having a diameter sd greater than second diameter d2. According to the illustrated example, first diameter d1 and secure zone diameter sd, are both greater than a maximum diameter md of device projecting member protuberance 495 (FIG. 4A), whereas second, smaller diameter d2 is about equal to maximum diameter md. FIG. 4B shows distal segment 562 of wire 560 extending in receptacle 62 and restrained in a similar manner as in receptacle 52 of tethering assembly 500, by a retainer zone 613, which, stops wire transition segment 563 from moving into shaft receptacle 62. FIG. 4B further illustrates the above-described pre-formed curvature of wire distal segment 562 relative to center-line RCL6 of shaft receptacle 62, and wire distal-most tip 56-DT extending in shaft receptacle passageway 623, according to the bias of spring member 550.

Figure 4C:
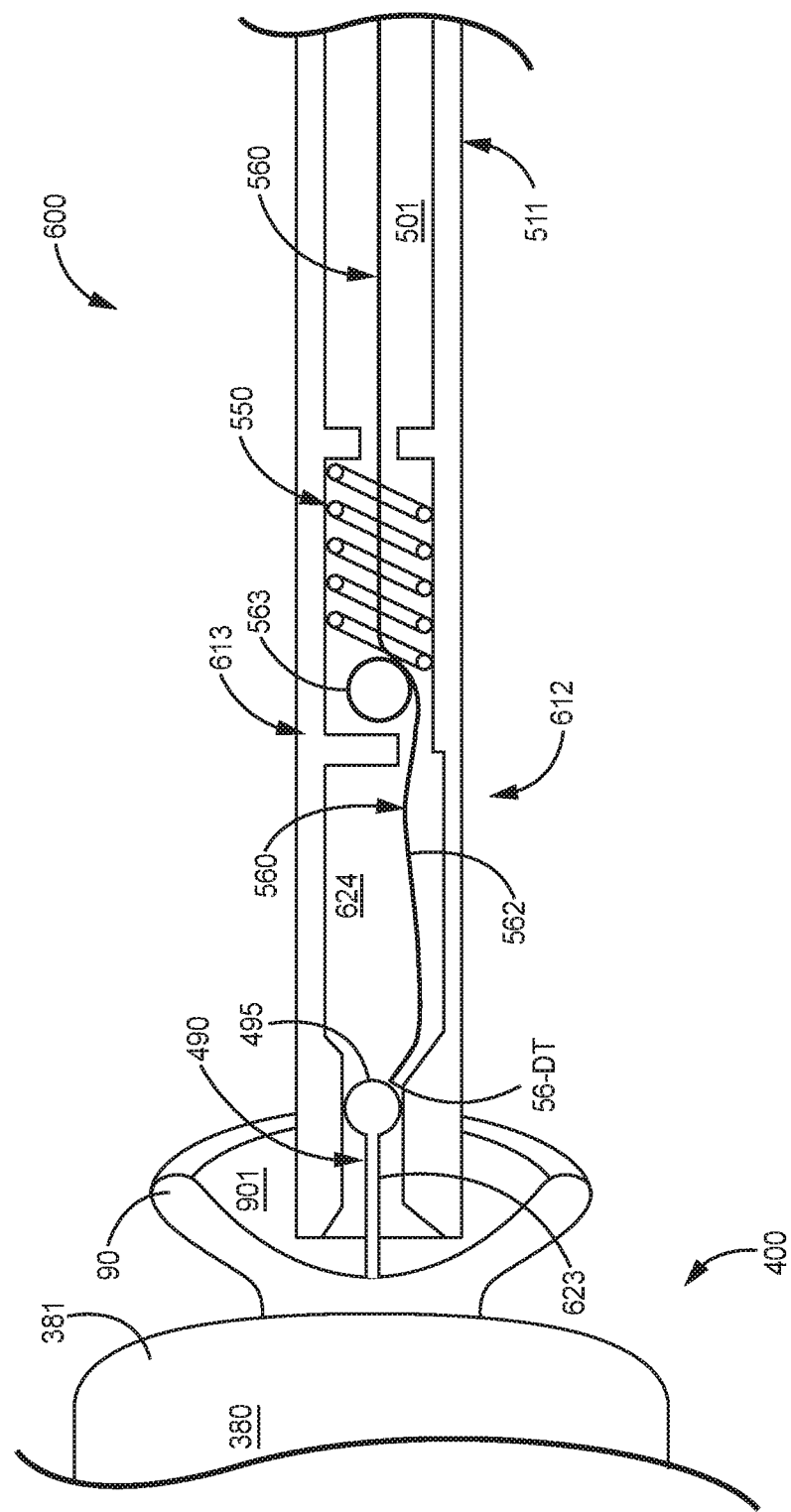
FIG. 4C is another longitudinal cross-section view of the portion of the tethering assembly and a portion of an implantable medical device included in the system of FIG. 4A.
Figure 4D:
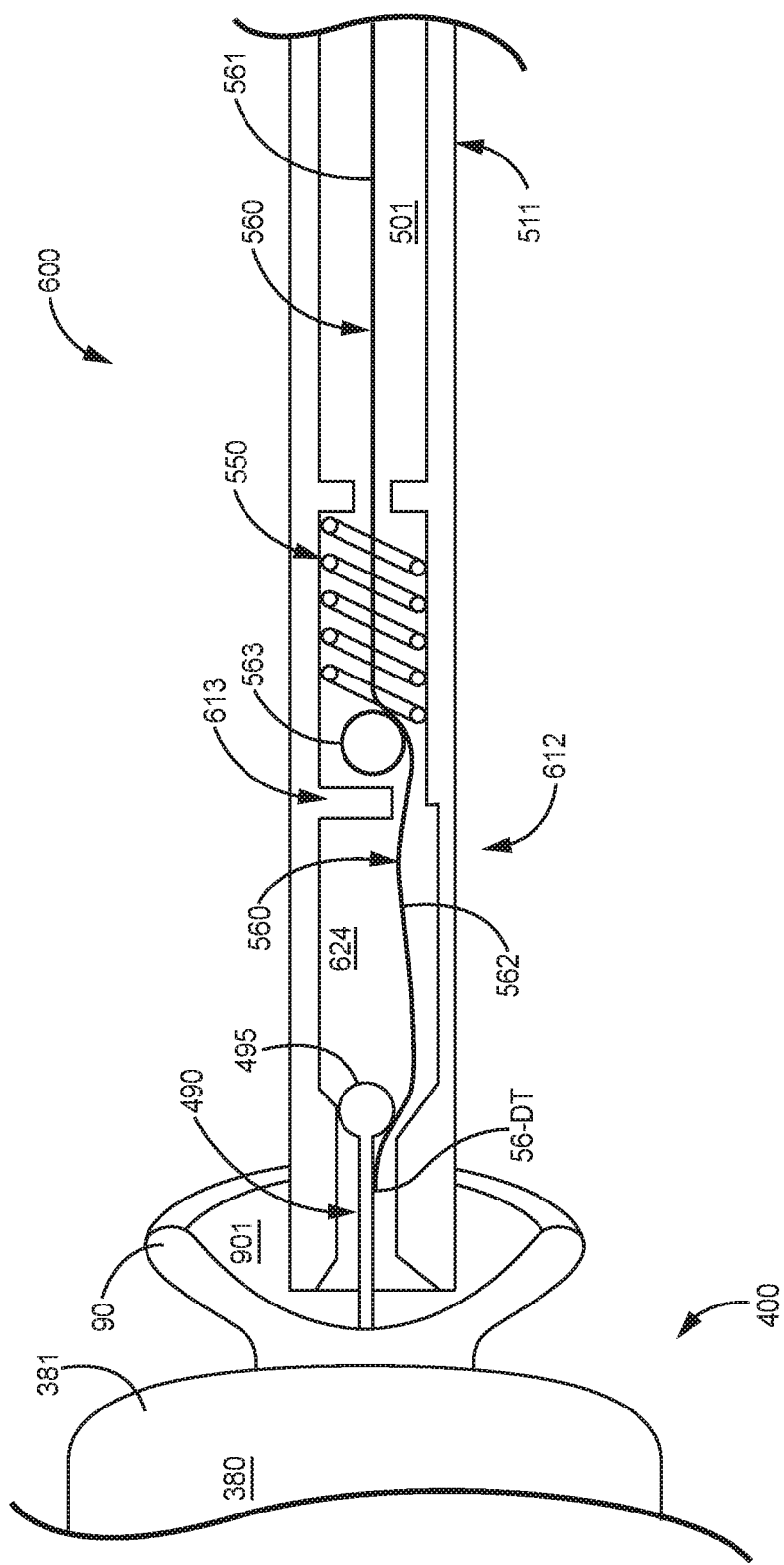
FIG. 4D is another cross-section view of the portions of the tethering assembly and the device of the system of FIG. 4A.

FIG. 4C is a longitudinal cross-section view that shows protuberance 495 of device projecting member 490, having been moved proximally through receptacle distal-most opening 622 and passageway 623 to confront wire distal-most tip 56-DT and push wire 560 proximally, against the bias of spring member 550. Then, as projecting member 490 continues to move proximally and pushes distal-most tip 56-DT into secure zone 624 of shaft receptacle 62, protuberance 495 of projecting member 490 is allowed to pass into secure zone 624 too. With reference to FIG. 4D, when protuberance 495 of device projecting member 490 comes into secure zone 624, wire distal-most tip 56-DT moves, according to the bias of the spring member 550, distally, alongside projecting member 490 and back into passageway 623 so that protuberance 495 of projecting member 490 seats against wire distal segment 562, in proximity to inflection point IP thereof. As in the securement of device 300 to tethering assembly 500, the protrusion of wire distal-most tip 56-DT into passageway 632 (lock position of wire distal segment 562), distal to device projecting member protuberance 495, blocks passageway 632, or effectively reduces diameter d2 of passageway 623 to one smaller than maximum diameter and of projecting member protuberance 495, and a mechanical interlock is created to secure device 400 to tethering assembly 600. To release device 400 from tethering assembly 600, proximal end 56-P of wire 560 may be engaged to move wire 560 proximally, relative to shaft 610 and device 400, so that wire distal-most tip 56-DT is retracted past projecting member protuberance 495 and into secure zone 624 (release position of wire distal segment 562) where tip 56-DT no longer blocks passageway 623. With reference back to FIG. 3A, handle 570 may be employed in tethering assembly 600 so wire proximal end 56-P is engaged via handle second part 572 as described above.

Turning now to the plan view of FIG. 5A, the aforementioned delivery catheter assembly 800 is shown included in a system, according to some examples, with any of the above described examples of tethering assemblies 500, 600, to which the corresponding implantable medical device 300, 400 is secured, as described above. FIG. 5A illustrates delivery catheter assembly 800 including an elongate outer tubular member 850, an elongate inner tubular member 820, around which outer tubular member 850 extends in sliding engagement, and a handle assembly 870, which has a proximal port opening 807 in communication with inner tubular member 820 to allow passage of tethering assembly 500, 600 therethrough. Delivery catheter assembly 800 may have a very similar construction as that of the tool described in the commonly assigned U.S. Pat. No. 9,526,522, except that the tethering assembly described in the '668 reference is not included to make way for any of the examples of tethering assemblies 500, 600 disclosed herein.

FIG. 5A further illustrates tethering assembly 500, 600 including a two-part handle 970, in lieu of handle 570 described above, wherein shaft proximal portion 511 and handle 970 protrude from catheter proximal port opening 807. Handle 970 is described in greater detail below. According to the illustrated example, tethering assembly 500, 600 has been loaded into catheter 800, shaft distal portion 512, 612 first, through opening 807, so that shaft distal portion 512, 612 protrudes out from a distal opening 802 of a lumen 805 of outer tubular member 850 for an operator to secure device 300, 400 to tethering assembly 500, 600 by the means described above. A second part 972 of tethering assembly handle 970 is shown in a first position, relative to a first part 971 of handle 970, which corresponds to the above-described lock position of tethering assembly wire 560. According to those examples in which wire 560 is spring-biased, second part 972 remains in the first position while the operator secures device 300, 400 to tethering assembly 500, 600, so that the operator only moves second part 972 to a second position, for example, by rotating second part 972 around a longitudinal axis of handle 970, relative to first part 971, per arrow X, which pulls wire 560 against the spring-bias, when the operator desires to release device 300, 400 from the securement, as described in greater detail below. But, according to alternate examples in which wire is not spring-biased, the operator moves handle second part 972 to the second position, in order to retract wire distal segment 562 to the above described release position, at which wire distal-most tip 56-DT is located in receptacle secure zone 524, 624 (so as not to block receptacle passageway 54, 623), so that the operator can move device projecting member 395, 495 into secure zone 524, 624. Then, in these examples without the spring-bias, in completing the securement of device 300, 400 to tethering assembly 500, 600, the operator moves handle second part 972 back to the first position to move wire distal segment 562 distally alongside projecting member 395, 495, which the operator holds in secure zone 524, 624, and back into the lock position with wire distal-most tip 56-DT blocking passageway 54, 623.

With further reference to FIG. 5A, outer tubular member 850 of catheter assembly 800 is shown retracted relative to inner tubular member 820 for the securing of device 300, 400 to tethering assembly 500, 600, for example, via a first control member 875 of handle assembly 870, which is coupled to outer tubular member 850. Once device 300, 400 is secured, the operator moves control member 875, per arrow A, so that outer tubular member 850 moves distally relative to the secured device 300, 400 and inner tubular member 820, to load device 300, 400 within lumen 805 of outer tubular member 850 at a distal end 852 thereof, for example, as shown in the cross-section view of FIG. 5B.

FIG. 5B illustrates device 300, 400 having passed through distal-most opening 802 of outer tubular member lumen 805 so that each of a plurality of super-elastic fingers 35, which form a fixation member of device 300, 400, are elastically deformed from a relaxed condition, shown in FIG. 5A, to an extended condition, in which a free end of each finger 35 extends distally away from distal end 382 of device housing 380. According to an example, fixation fingers 35 are integrally formed with one another, having been cut from Nitinol tubing, according to methods known in the art. After cutting the Nitinol tubing, fingers 35 may be shaped by bending and holding fingers 35 in the illustrated curvature (FIG. 5A) while heat treating, according to methods known to those skilled in the art. Fixation fingers 35 may be mounted to distal end 382 of device housing 380, for example, in a manner similar to that described for a fixation component 102 in a commonly assigned United States Patent Application 2012/0172690, which description is hereby incorporated by reference.

Figure 5C:
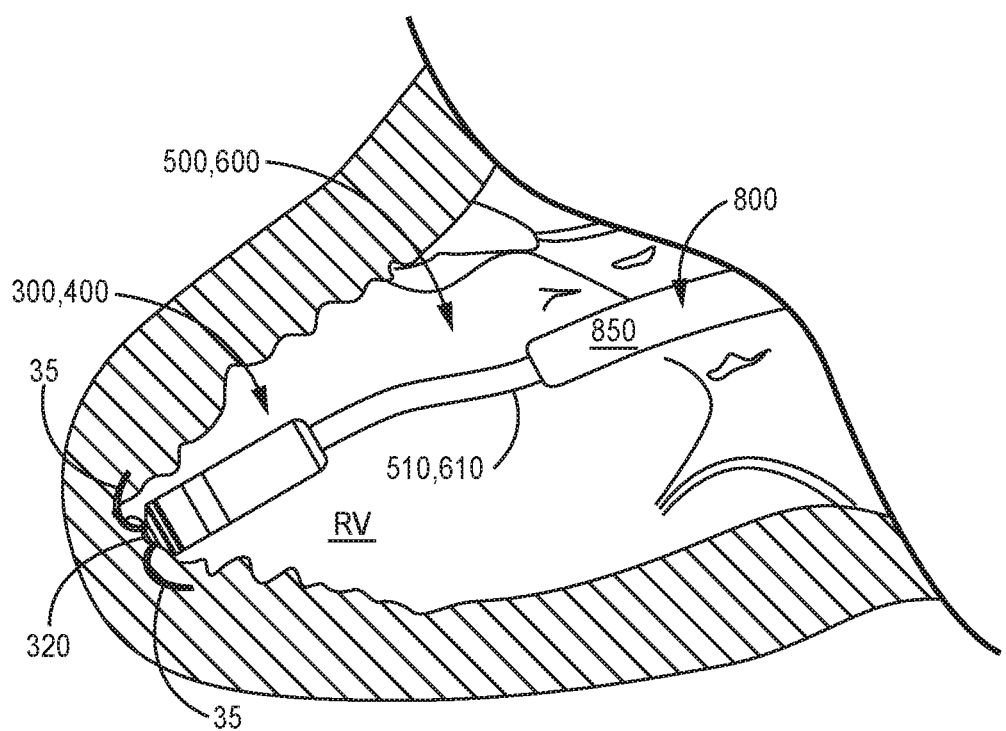
FIG. 5C is a schematic depicting the device implanted and still secured by the tethering assembly.

According to the illustrated example, after the operator has moved catheter assembly 800 (with device 300, 400 loaded therein and secured to tethering assembly 500, 600) into proximity with a target implant site, and positioned distal-most opening 802 in close proximity thereto, the operator may retract outer tubular member 850 relative to device 300, 400 and tethering assembly 500, 600 so that fixation fingers 35 are released to pierce into tissue at the implant site and thereby secure electrode 320 of device 300, 400 in intimate tissue contact. With further reference to FIG. 5B handle assembly 870 of catheter assembly 800 includes a second control member 876 for an optional steering assembly, which may be useful in navigating catheter assembly 800 into proximity with the implant site. For the purposes of illustration, FIG. 5C is a schematic depicting device 300, 400 implanted at a site in a right ventricle RV of a patient's heart. The illustrated implant site is exemplary, as various other sites are possible for implant of device 300, 400, as well as for the other types of devices mentioned above. FIG. 5C shows device 300, 400 still secured to tethering assembly 500, 600 and catheter assembly 800 withdrawn a distance from the implant site for a preliminary evaluation of the performance of the implanted device 300, 400 at the site, for example, cardiac pacing thresholds of electrode 320. In some examples, device 300 includes a steroid-eluting member (not shown), for example, mounted in, or around electrode 320, which is useful for reducing inflammation of the pierced tissue to maintain effective and efficient pacing via electrode 320.

The operator may also evaluate the fixation of device 300, 400, via fixation fingers 35, at the implant site by applying a tug, or pull force through tethering assembly shaft 510, 610. If the operator determines that device 300, 400 should be located at an alternative site, the operator can apply an even greater pull force through tethering assembly shaft 510, 610, for example, up to about 10 pounds, to disengage device fixation fingers 35 from the site while advancing outer tubular member 850 of catheter assembly 800 to re-load device 300, 400 for deployment at another site. It should be noted that when the operator applies the pull forces to tethering assembly shaft 510, 610 by gripping tethering assembly handle first part 571, 971 (FIGS. 3A, 5A), tethering assembly wire 560 is isolated from the pull force so that wire distal segment 562 remains in the lock position to keep device 300, 400 secured to tethering assembly 500, 600.

Suitable constructions for tethering assembly shaft 510, 610 are those that allow for this isolation of wire 560 from the aforementioned pull forces, and also provide sufficient tensile strength and kink-resistance, for the handling thereof. Shaft 510, 610 should also be constructed with an increased flexibility along a length that extends in close proximity to distal portion 512, 612, so that when the implanted device 300, 400 is being evaluated, as illustrated in FIG. 5C, a stiffness of shaft 510, 610 does not interfere with the intimate tissue contact of electrode 320. According to examples, proximal portion 511 of tethering assembly shaft 510, 610 is formed by a flexible metal hypo-tube of a coiled or braided medical grade stainless steel wire, which may have an overlay of a relatively flexible medical grade polymer, for example, PEBAX® 3533 or similar. Shaft distal portion 512, 612 and retainer zone 513, 613 may be integrally formed from a relatively hard medical grade polymer, for example, PEBAX® 7233 or similar, or from a medical grade stainless steel. The shaft proximal and distal portions may be joined together by adhesive and/or thermal bonding, according to methods known in the art.

After the operator is satisfied with the implant site for device 300, 400, the operator may release the implanted device 300, 400 from tethering assembly 500, 600 by moving handle second part 972, as described above. Then, when the operator has withdrawn catheter assembly 800 and tethering assembly 500, 600 from the patient's body, both may again be employed, in the same fashion as described above, to deliver another device, if necessary, to another target implant site within the patient's body.

Figure 6:
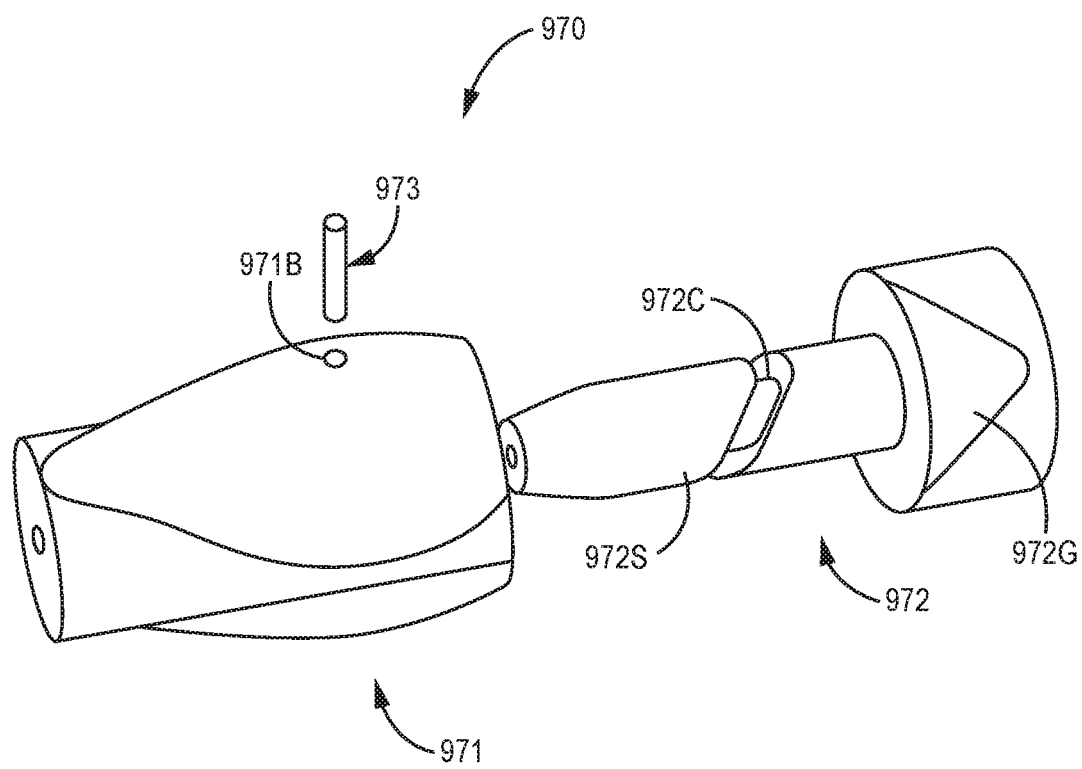
FIG. 6 is an exploded perspective view of an example handle for a tethering assembly, according to aspects of this disclosure.

FIG. 6 is an exploded perspective view of tethering assembly handle 970. FIG. 6 illustrates handle second part 972 including a grip region 972G and a shank 972S extending therefrom, wherein shank 972S is configured to fit within a lumen (not shown) of handle first part 971 and includes a channel 972C formed therein. FIG. 6C further illustrates tethering assembly handle 970 including a pin member 973, which when fitted within a bore 971B of handle first part 971, extends into the lumen thereof to interlock with second part channel 972C. According to the illustrated example, channel 972C extends helically around shank 972S, so that when second part grip region 972 is rotated, as described above, handle second part 972 moves longitudinally between the aforementioned first and second positions. Handle 970 may be formed from any suitable medical grade metal or hard plastic.

In the foregoing detailed description, the invention has been described with reference to specific examples. However, it may be appreciated that various modifications and changes can be made without departing from the scope of the invention as set forth in the appended claims.

What is claimed is:

1. A system comprising:
    an implantable medical device comprising:
        a hermetically sealed housing that contains one or more processors for delivering a pacing therapy; and
        a projecting member joined to the hermetically sealed housing; and
    a tethering system comprising:
        a shaft that extends longitudinally between a distal end and a proximal end;
        an attachment component coupled to the distal end of the shaft, the attachment component defining a receptacle comprising a relief and a secure zone opposing the relief, wherein the secure zone is configured to receive the projecting member of the implantable medical device, wherein the attachment component defines a passageway that provides access to the receptacle and that is narrower than the receptacle, wherein the attachment component is configured to be coupled to the projecting member of the implantable medical device; and
        a wire extending in sliding engagement within the shaft between a first position in which a distal most tip of the wire extends into the passageway of the receptacle thereby narrowing the passageway and a second position in which the distal most tip retracts into the receptacle, the wire being moveable from the first position to the second position and from the second position to the first position, wherein at least a portion of a distal segment of the wire is configured to deflect into at least a portion of the relief as the projecting member of the implantable medical device enters the secure zone.

2. The system of claim 1, wherein the shaft is composed of a flexible material that transfers torque applied at the proximal end of the shaft to the attachment component coupled to the distal end of the shaft.

3. The system of claim 2, wherein the flexible material comprises a hollow stranded cable, and wherein for the wire passes through the hollow stranded cable.

4. The system of claim 1, wherein the tethering system further comprises an electrically insulating layer that covers the shaft over at least a portion of the shaft.

5. The system of claim 1, wherein the wire has a diameter of approximately 0.006 of an inch and wherein the shaft has an inside diameter of approximately 0.0095 of an inch.

6. The system of claim 5, wherein the wire is composed of a flexible material such that application of force to the distal end of the wire results in deflection of the wire within the shaft.

7. The system of claim 1, wherein the wire has a circular or ovoidal cross-sectional shape.

8. The system of claim 1, wherein the distal most tip of the wire is displaced approximately 0.100 of an inch between the first position and the second position.

9. The system of claim 1, wherein the secure zone includes an offset such that the receptacle increases in size from a distal end of the receptacle nearer the passageway to a proximal end of the receptacle nearer the shaft, the offset configured to accommodate horizontal and vertical movement of the projecting member of the implantable medical device as the projecting member is inserted into the receptacle from the distal end of the receptacle to the proximal end of the receptacle.

10. The system of claim 1, wherein the passageway includes a groove at the base of the passageway, the wire being disposed within the groove, the groove having a depth that is less than the thickness of the wire.

11. The system of claim 1, wherein the passageway has an opening at the distal end that tapers down in size.

12. The system of claim 1, wherein the tethering system further comprises:
    a release assembly being coupled to the proximal end of the shaft and to a proximal end of the wire, wherein actuation of the release assembly causes the wire to move from the first position to the second position.

13. The system of claim 1, further comprising a stiffening component covering at least a portion of the shaft.

14. The tethering assembly system of claim 1, further comprising a biasing member that is positioned relative to the receptacle and configured to bias the projecting member of the implantable medical device toward the passageway.

15. The system of claim 14, wherein the biasing member comprises a sleeve that at least partially covers the attachment component.

16. The system of claim 1, wherein the projecting member comprises an oblong cavity, and wherein the attachment component comprises an oblong shape configured to fit at least partially within the oblong cavity.

17. The system of claim 1, wherein the projecting member comprises a pin, and wherein the passageway is sized to allow the pin to move into the receptacle when the wire is located in the second position and to prevent the pin from moving out of the receptacle when the wire is located in the first position.

18. The system of claim 1, wherein the projecting member extends from a proximal end of the implantable medical device, and wherein the passageway is sized to allow the projecting member to move into the receptacle when the wire is located in the second position and to prevent the projecting member from moving out of the receptacle when the wire is located in the first position.

\* \* \* \* \*